United States Patent [19]
Kendall et al.

[11] Patent Number: 5,939,033
[45] Date of Patent: *Aug. 17, 1999

[54] GAS/VAPOR DELIVERY FROM SOLID MATERIALS

[75] Inventors: Richard Jed Kendall, San Clemente; Xiaolan Chen, Irvine; Michael Hahs, San Clemente; Paul Taylor Jacobs, Trabuco Canyon; Szu-Min Lin, Laguna Hills; Robert M. Spencer, San Juan Capistrano; Harold R. Williams, San Clemente, all of Calif.

[73] Assignee: Johnson & Johnson Medical, Inc., Irvine, Calif.

[*] Notice: This patent is subject to a terminal disclaimer.

[21] Appl. No.: 08/744,741

[22] Filed: Oct. 28, 1996

Related U.S. Application Data

[63] Continuation-in-part of application No. 08/549,425, Oct. 27, 1995, Pat. No. 5,667,753.

[51] Int. Cl.$^6$ ....................................................... A61L 2/20
[52] U.S. Cl. .............................. 422/305; 422/28; 422/29; 422/37; 422/306; 422/292; 43/125; 428/35.7; 428/35.8; 428/35.9; 428/36.5; 428/36.6; 428/36.7; 392/386; 392/390
[58] Field of Search .................................. 422/28, 29, 37, 422/123, 125, 261, 265, 305, 306, 292; 43/125; 428/35.7–35.9, 36.5, 36.6, 36.7; 392/386, 390

[56] References Cited

U.S. PATENT DOCUMENTS

| | | |
|---|---|---|
| 970,898 | 9/1910 | Eklund . |
| 2,120,430 | 1/1938 | Rieche et al. . |
| 2,986,448 | 5/1961 | Gates et al. . |

(List continued on next page.)

FOREIGN PATENT DOCUMENTS

| | | |
|---|---|---|
| 0679407 A2 | 11/1995 | European Pat. Off. . |
| 60-135056 | 12/1983 | Japan . |
| 04343850 | 11/1992 | Japan . |
| 1681860A1 | 1/1989 | U.S.S.R. . |
| 1681860 | 10/1991 | U.S.S.R. . |
| 1509184 | 5/1978 | United Kingdom . |
| 2223680 | 4/1990 | United Kingdom . |
| WO 92/17158 | 10/1992 | WIPO . |

OTHER PUBLICATIONS

Sax, N. Irving, Dangerous Properties of Industrial Materials, pp. 772 & 817 (1975).

Windholz, et al. The Merck Index, An Encyclopedia of Chemicals, Drugs and Biologicals, 1983; p. 538.

Chemical Abstracts, vol. 95, 1981, p. 444.

Lu, Chia–Si, et al., ; The Crystal Structure of the Urea–Hydrogen Peroxide Addition Compound CO (NH$_3$ )$^3$H$_2$O$_2$ ; Jun. 1941; pp. 1507–1513.

Titova, K.V. Kolmakova E. I. ; Zhurnal Neorganicheskoi Khimii, vol. 30, 1985, Issue 9, pp. 2222–2227; "Potassium Carbonate Peroxyhydrate (K$_2$CO$_3$3H$_2$O$^2$)". (In Russian with English translation).

*Primary Examiner*—Elizabeth McKane
*Assistant Examiner*—Fariborz Moazzam
*Attorney, Agent, or Firm*—Knobbe, Martens, Olson & Bear, LLP

[57] ABSTRACT

A system to deliver gas/vapor from solid materials. Specifically, the delivery system for the use of gas or vapor released from a solid material, such as a non-aqueous/solid hydrogen peroxide complex. The system is comprised of a delivery system that is configured to receive a plurality of disks containing the solid material and provide these disks into an injector. The injector heats the disks to produce a gas or vapor that is then provided into a chamber. The sterilization process can be done by gas or vapor alone, or in combination with plasma or ultra violet radiation. In particular, a control system automatically induces the delivery system to provide the injector with a disk and then remove the disk once the injection sequence is complete.

24 Claims, 22 Drawing Sheets

U.S. PATENT DOCUMENTS

| | | |
|---|---|---|
| 3,306,493 | 2/1967 | Szajna . |
| 3,376,110 | 4/1968 | Shiraelf et al. . |
| 3,480,557 | 11/1969 | Shiraelf et al. . |
| 3,494,726 | 2/1970 | Barasch . |
| 3,650,038 | 3/1972 | Alessi et al. . |
| 3,650,705 | 3/1972 | Majewski . |
| 3,866,347 | 2/1975 | Schoom .................................. 43/125 |
| 3,870,783 | 3/1975 | Hall et al. . |
| 4,005,234 | 1/1977 | Stroupe .................................. 428/35.9 |
| 4,051,059 | 9/1977 | Bowing et al. . |
| 4,075,116 | 2/1978 | Mesaros . |
| 4,139,093 | 2/1979 | Holmes . |
| 4,169,123 | 9/1979 | Moore et al. . |
| 4,169,124 | 9/1979 | Forstrom et al. . |
| 4,178,263 | 12/1979 | Priddy . |
| 4,199,548 | 4/1980 | Kaiho et al. .......................... 43/125 |
| 4,251,714 | 2/1981 | Zobele . |
| 4,366,125 | 12/1982 | Kodera et al. . |
| 4,395,261 | 7/1983 | Lutz .......................................... 8/111 |
| 4,437,567 | 3/1984 | Jeng . |
| 4,458,009 | 7/1984 | Weyde et al. . |
| 4,588,874 | 5/1986 | Napierski ............................... 392/390 |
| 4,597,218 | 7/1986 | Friemel et al. ....................... 43/131 |
| 4,637,894 | 1/1987 | Smidrkal et al. . |
| 4,642,165 | 2/1987 | Bier . |
| 4,643,876 | 2/1987 | Jacobs et al. . |
| 4,717,544 | 1/1988 | Calceterra et al. . |
| 4,744,951 | 5/1988 | Cummings et al. . |
| 4,756,882 | 7/1988 | Jacobs et al. . |
| 4,797,255 | 1/1989 | Hatanaka et al. . |
| 4,889,689 | 12/1989 | Tsao . |
| 4,908,188 | 3/1990 | Jefferis, III et al. . |
| 4,943,414 | 7/1990 | Jacobs et al. . |
| 4,956,145 | 9/1990 | Cummings et al. . |
| 4,981,662 | 1/1991 | Dougherty . |
| 5,008,093 | 4/1991 | Merianos . |
| 5,008,106 | 4/1991 | Merianos . |
| 5,030,380 | 7/1991 | Moschner et al. . |
| 5,039,495 | 8/1991 | Kutner et al. . |
| 5,077,047 | 12/1991 | Biss et al. . |
| 5,087,418 | 2/1992 | Jacob . |
| 5,115,166 | 5/1992 | Campbell et al. . |
| 5,122,354 | 6/1992 | Tsuji et al. . |
| 5,160,700 | 11/1992 | Anderson et al. ..................... 422/34 |
| 5,176,884 | 1/1993 | Taschner et al. . |
| 5,180,614 | 1/1993 | Escabasse ............................ 428/34.2 |
| 5,183,901 | 2/1993 | Login et al. . |
| 5,206,385 | 4/1993 | Login et al. . |
| 5,209,909 | 5/1993 | Siegel et al. . |
| 5,211,927 | 5/1993 | Itani et al. . |
| 5,228,569 | 7/1993 | House . |
| 5,266,275 | 11/1993 | Faddis . |
| 5,281,401 | 1/1994 | Bryson, Sr. . |
| 5,364,602 | 11/1994 | Leduc . |
| 5,388,177 | 2/1995 | Ono et al. ............................. 392/386 |
| 5,399,314 | 3/1995 | Samuel et al. . |
| 5,443,801 | 8/1995 | Langford . |
| 5,445,792 | 8/1995 | Rickloff et al. . |
| 5,508,009 | 4/1996 | Rickloff et al. . |

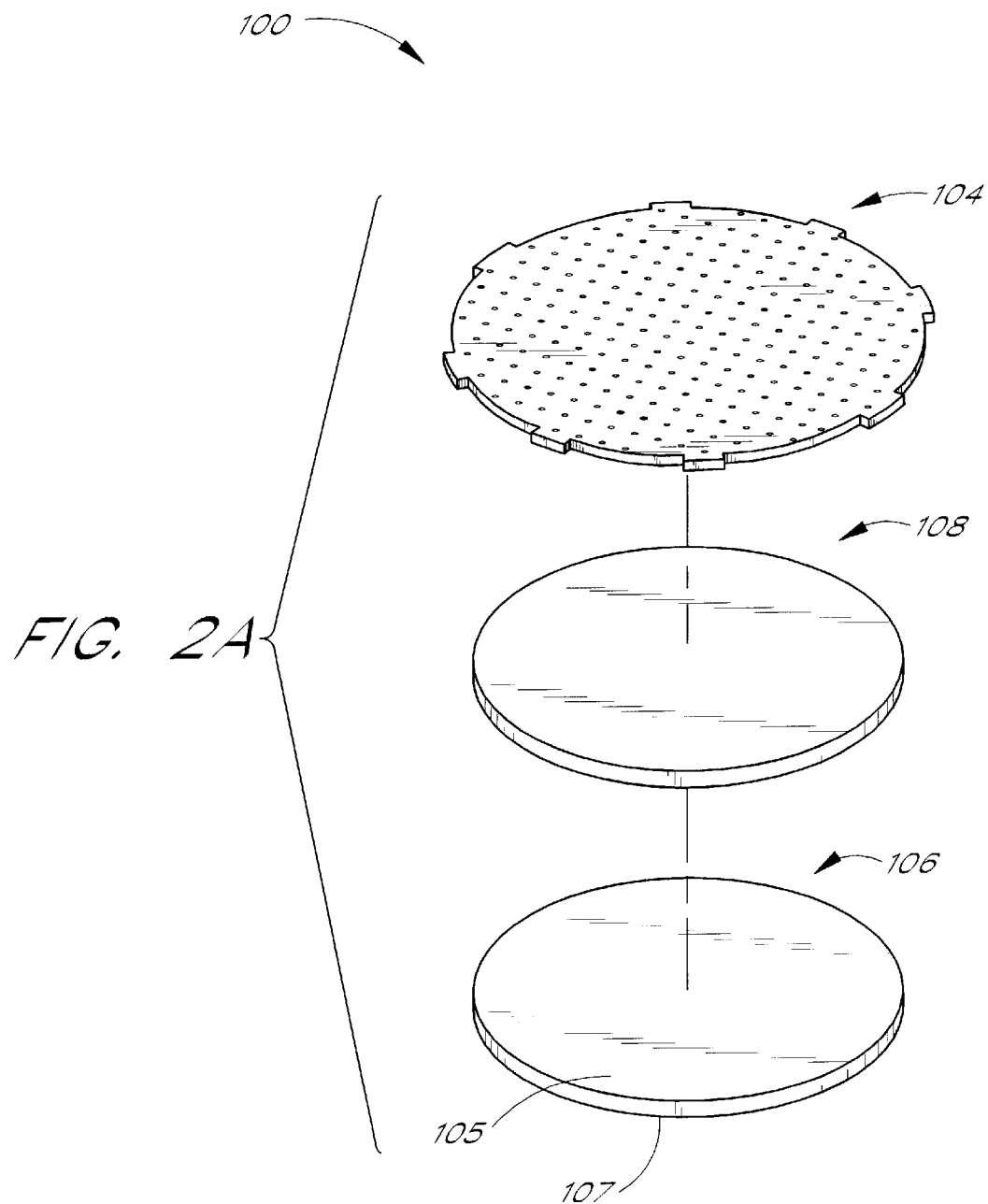

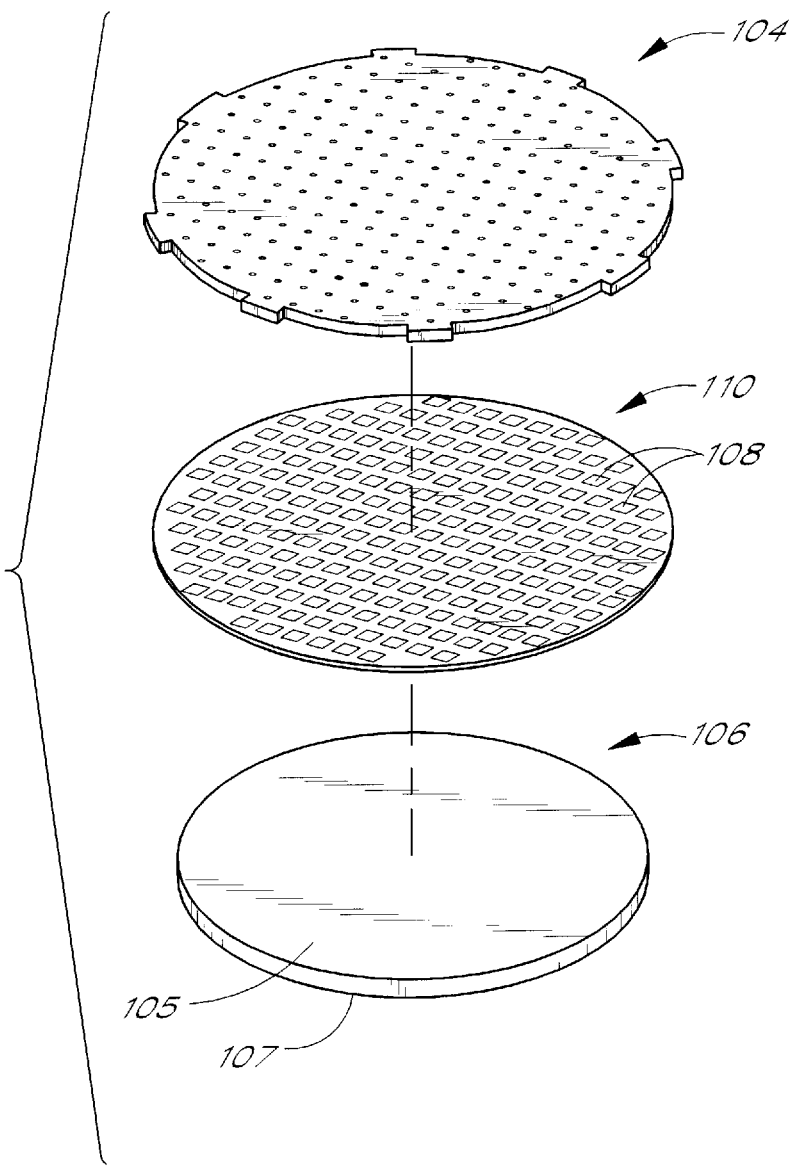

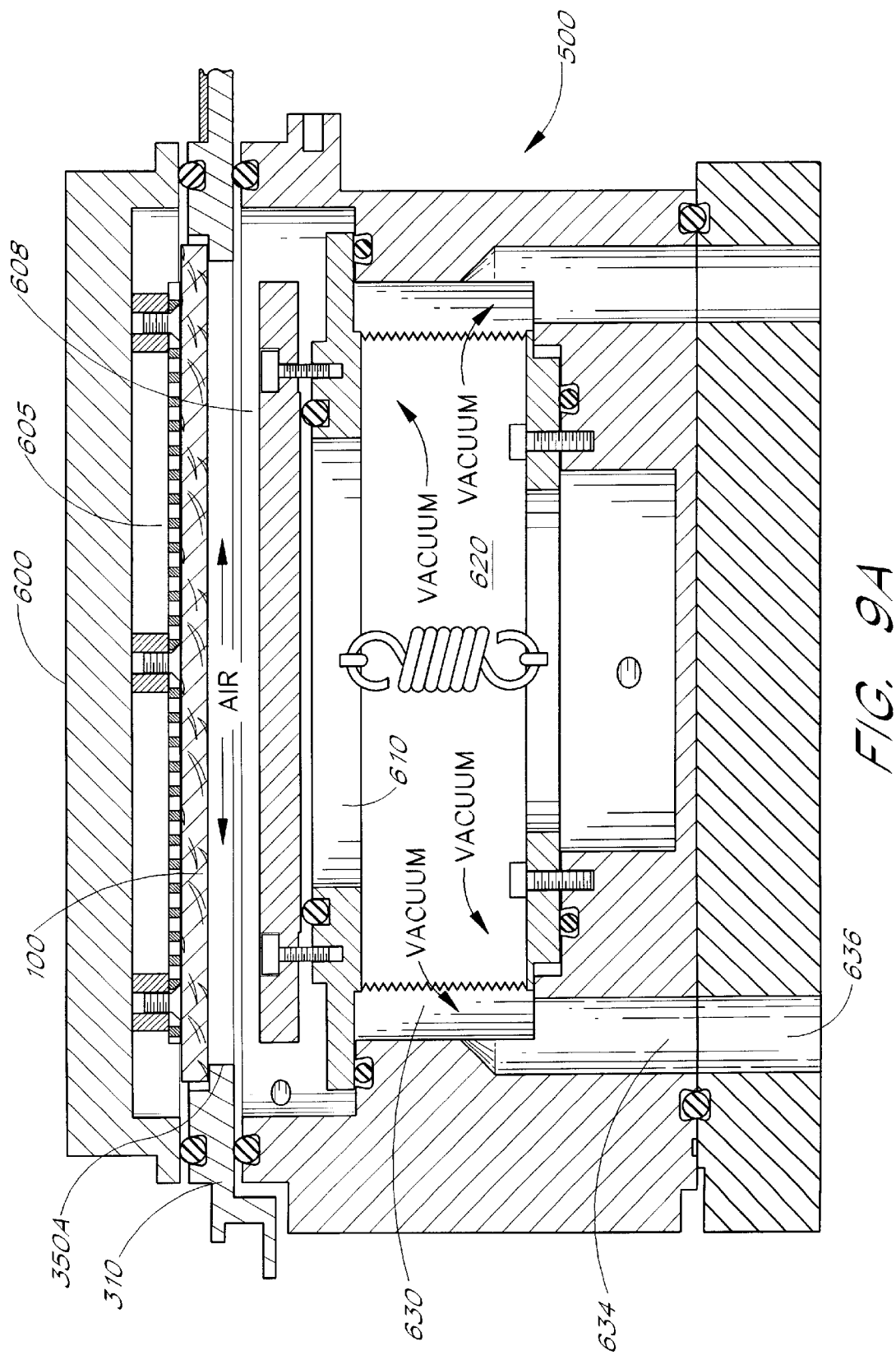

GAS/VAPOR DELIVERY FROM SOLID MATERIALS

RELATED APPLICATION

This application is a continuation-in-part of application Ser. No. 08/549,425, filed Oct. 27, 1995 now U.S. Pat. No. 5,667,753.

BACKGROUND OF THE INVENTION

1. Field of the Invention

The present invention generally relates to techniques using hydrogen peroxide released from hydrogen peroxide complexes for sterilizing articles such as medical instruments and materials.

2. Description of the Related Art

Modern medical and dental practices require the use of aseptic materials and devices, i.e., the materials and devices must be generally free from germs, bacteria, etc., and many of these devices are meant for repeated use. However, in order to achieve this asepsis, efficient sterilization processes are needed for treatment of reusable materials and devices. These processes are needed not only at hospitals and dental offices, but also at the manufacturers of these materials and devices.

Medical instruments have traditionally been sterilized using either heat, as is provided by steam, or a chemical, such as formaldehyde or ethylene-oxide gas or vapor state. Each of these methods has drawbacks. Many medical devices, such as fiber optic devices, endoscopes, power tools, etc., are sensitive to heat, moisture, or both. Formaldehyde and ethylene oxide are both toxic gases that pose a potential hazard to health care workers. Problems with ethylene oxide are particularly severe, because its use requires long aeration times to remove the gas from articles that have been sterilized. This makes the sterilization cycle time undesirably long. In addition, both formaldehyde and ethylene oxide require the presence of a substantial amount of moisture in the system. Thus, the device to be sterilized must be humidified before the chemical is introduced or the chemical and moisture are introduced simultaneously. Moisture plays a role in sterilization with a variety of other chemicals in the gas or vapor state, in addition to ethylene oxide or formaldehyde.

Sterilization using hydrogen peroxide vapor has been shown to have some advantages over other chemical sterilization processes, and the combination of hydrogen peroxide with plasma provides additional advantages. Hydrogen peroxide vapor can be generated from aqueous hydrogen peroxide solutions or from solid hydrogen peroxide complexes. However, the use of hydrogen peroxide in aqueous solutions of hydrogen peroxide to generate hydrogen peroxide vapor for sterilization may cause problems. At higher pressures, such as atmospheric pressure, excess water in the system can cause condensation. Thus, the relative humidity in the sterilization enclosure must be reduced before introducing the aqueous hydrogen peroxide vapor.

The sterilization of articles containing diffusion-restricted areas, such as long narrow lumens, presents a special challenge for hydrogen peroxide vapor that has been generated from an aqueous solution of hydrogen peroxide. The first problem arises because water has a higher vapor pressure than hydrogen peroxide and will vaporize faster than hydrogen peroxide from an aqueous solution. Another problem is that water has a lower molecular weight than hydrogen peroxide and will diffuse faster than hydrogen peroxide in the vapor state. Therefore, when an aqueous solution of hydrogen peroxide is vaporized, the water reaches the items to be sterilized first in a higher concentration. The water vapor, therefore, becomes a barrier to the penetration of hydrogen peroxide vapor into diffusion restricted areas, such as small crevices and long narrow lumens.

This problem cannot be solved by removing water from the aqueous solution and using more concentrated hydrogen peroxide, since concentrated solutions of hydrogen peroxide, i.e., greater than 65% by weight, can be hazardous due to the oxidizing nature of the solution. The shortcomings of aqueous hydrogen peroxide sterilizers of the prior art are overcome by using a non-aqueous source of hydrogen peroxide which releases a non-aqueous hydrogen peroxide vapor. In these processes, a solid peroxide complex is heated in a vaporizer and the vapor is diffused into the sterilization chamber.

SUMMARY OF THE INVENTION

One aspect of the present invention is a package for containing a solid material which releases gas or vapor upon heating. This package includes a gas permeable membrane, and the solid material which releases gas or vapor upon heating. The solid material is sealed underneath the gas permeable membrane. The solid material can be in the form of a powder, tablet or dried slurry. One exemplary type of solid material would be a hydrogen peroxide complex. Other exemplary types of solid material include a hydrate complex or an ammonia complex. The solid material preferably releases gas or vapor at a temperature within the range 20–300° C., more preferably within the range 25–250° C. In one embodiment, the package includes a conductive foil, with the solid material between the gas permeable membrane and the conductive foil. The foil preferably has a reflective outer surface configured to reflect radiant heat away from the solid material. In another embodiment, the package includes an impermeable membrane, with the solid material between the gas permeable membrane and the impermeable membrane. Exemplary materials for the impermeable membrane of this embodiment include Mylar™, polycarbonate and PTFE material. Preferably, the impermeable membrane is transparent to radiation, such as infra-red, microwaves or radio frequency. Where the impermeable material is transparent to radiation, a susceptor can be added which is excitable by the radiation. Such a susceptor can be a screen adjacent the solid material, where the screen provides pockets holding the solid material. A susceptor, such as a metallic powder or carbon black can also be mixed with solid material. In embodiments having a foil or impermeable membrane, an adhesive material, such as a tape, on the inner surface of the foil or impermeable material can be provided to which the solid material is adhered. The foil or impermeable material can also be embossed to provide pockets which hold the solid material. Exemplary embossing patterns include hexagonal or rectilinear patterns. An impermeable material can also be sealed over the permeable membrane, such that the solid material will be sealed within the package until the impermeable material is ruptured. Preferably, the melting point of the gas permeable membrane is higher than the release temperature of the solid material. A perforated material or screen can optionally be included outside of the gas permeable membrane. Such a perforated material or screen is especially useful in packages where the gas permeable membrane is of glass filter material. The package can also include a screen adjacent the solid material. Such a screen can provide pockets holding the solid material. The screen can be conductive of heat so as to improve heat transfer to the solid material. The package can be incorporated into a support which is capable of being handled. The support can be configured to form a seal to enclose the solid material. Where the support forms a seal, the support can be provided with perforations around the package so as to permit gas or vapor released from the solid material and through the gas permeable membrane to be delivered to an opposing side of the package. The gas permeable material can be heat-sealed or sealed using an adhesive to enclose the solid material.

Another aspect of the present invention relates to a cartridge housing. The cartridge housing includes a plurality of packages for containing a solid material which releases gas or vapor upon heating. Each of the packages includes gas permeable membrane, and the solid material which releases gas or vapor upon heating. The solid material is sealed within the gas permeable membrane. The plurality of packages are preferably stacked so that each of the packages can be activated one at a time. Each of the packages can have at least one edge joined to at least one edge of another of the packages, so that the plurality of packages can be folded in a Z-fold or rolled. If the packages are rolled, they are preferably rolled onto a core. The packages can also be arranged around the periphery of a disk. In some embodiments, the packages are sealed within the housing. In such embodiments, the cartridge can be configured to trap gas or vapor released from the solid material within the housing, such as by providing an impermeable material sealed over the housing, such that the packages will be sealed within the housing until the impermeable material is ruptured. The cartridge housing can be adapted to protect the packages therewithin from a heating source.

Still another aspect of the invention relates to a method of releasing gas or vapor from a solid material capable of releasing the gas or vapor. The method includes providing the solid material sealed within a gas permeable material, and heating the solid material, thereby releasing the gas or vapor through the gas permeable material. The solid material can advantageously be a hydrogen peroxide complex. Thus, the method can also include contacting hydrogen peroxide released from the complex with an object to be disinfected or sterilized. If disinfection or sterilization is desired, the method can also include contacting the object with plasma or ultraviolet radiation. The solid material can be sealed between the gas permeable material and a conductive foil when the heating step comprises conductive heating. The heating step can also comprise irradiative heating. For such methods, it is preferable that the solid material be sealed between the gas permeable material and an impermeable material. The irradiative heating can use radiation such as infra-red, microwaves or radio frequency. The wavelength of the irradiation is preferably selected to excite the solid material to release the gas or vapor. In a preferred embodiment, the solid material is in contact with a susceptor which is excitable by radiation causing the irradiative heating. The susceptor could be a screen adjacent the solid material or a material mixed with the solid material. Preferably, the wavelength of the irradiation is selected to excite the susceptor so as to cause it to be heated. The heating can also involve convection heating.

Yet another aspect of the invention relates to an injection system for conductively heating packages containing a solid material which releases gas or vapor upon heating. This system includes a housing with a gas permeable plate which is adapted to press on a first side of the package, an opening in the housing through which the package can be inserted, and a heatable surface which is adapted to press on a second side of the package away from the first side thereof. The gas permeable plate is preferably rigid, and the heatable surface is preferably mounted on a carriage adapted to move the heatable surface into contact with the second side of the package. The gas or vapor released from the solid material can be released into a first chamber, and the carriage provided with a seal adapted to create a passageway through which the gas or vapor released from the solid material can pass into a second chamber when the heatable surface is in contact with the second side of the package. When the heatable surface is not in contact with the second side of the package, the first and second chambers are preferably sealed from each other. The carriage can advantageously be adapted to move from a first position wherein the heatable surface is away from the package to a second position wherein the heatable surface is in contact with the package as a result of pressure differences between the first chamber and a bellows chamber. Thus, the system can also be provided with a spring to move the carriage from the second position to the first position when the pressure difference between the first chamber and the bellows chamber is approximately zero. As can be appreciated from the foregoing summary of the system, the opening is preferably sealable; however the opening need not be sealable. In one embodiment, the opening seals directly to the -package, and other embodiments, the opening seals to a support upon which the package is mounted or to a mechanism which carries the package.

Still one more aspect of the invention relates to a method of releasing gas or vapor from a package containing a solid material which releases gas or vapor upon heating. The method includes providing a housing with a gas permeable plate therein, inserting the package into an opening in the housing so as to place a first side of the package into an orientation facing the plate, pressing a heatable surface onto a second side of the package away from the first side thereof, thereby pressing said first side against the plate and heating the package so as to release gas or vapor therefrom. The second side of the package preferably comprises a conductive foil, wherein the conductive foil is heated by conductive heating from the heatable surface.

Yet one more aspect of the invention relates to a delivery system for delivering a plurality of packages containing a solid material capable of releasing gas or vapor upon heating, to an injection system. This aspect of the invention includes a source cartridge containing a plurality of the packages, an upper delivery member that has a first aperture configured to receive the source cartridge and a second aperture adapted to receive the destination cartridge, a lower delivery member that has at least one aperture that is configured to receive one or more of the packages from the source cartridge, the lower delivery member being movable so that the package can be positioned in an opening in the injection system, and further movable to deliver used packages to a destination. In a preferred embodiment, the destination is a destination cartridge for receiving the packages after they are used. In this embodiment, the upper delivery member preferably includes a second aperture adapted to receive the destination cartridge. Each of the upper and lower delivery members is preferably a carousel. The delivery system can also include a controller which induces the delivery system to provide a package to the injection system. The controller is preferably adapted to enable a vacuum source which is adapted to pneumatically attach and detach the packages thereto. Thus, the vacuum source can be enabled to retrieve and place the packages. In one preferred embodiment, the vacuum source makes use of suction cups to attach and detach the packages. In a preferred embodiment, the upper delivery member provides a single point of access to put in and take out the packages.

One more aspect of the invention relates to a method of delivering a plurality of packages containing a solid material capable of releasing gas or vapor upon heating to an injection system. This method includes (a) placing the plurality of packages in a source cartridge, (b) placing the source cartridge in a first aperture of an upper delivery member, (c) placing a destination cartridge in a second aperture of the upper delivery member, (d) moving a package from the source cartridge to an aperture in a lower delivery member, (e) moving the lower delivery member so as to position the package which has been moved to the aperture in the lower delivery member in an opening in the injection system, (f) releasing gas or vapor from the package in the injection system, and (g) moving the lower delivery member so as to deliver the package from which gas or vapor has been released to the destination cartridge. Steps (e) and (g) preferably comprise rotational movement of the lower delivery member, and can be accomplished by activating a controller in order to effect movement of the lower delivery member. The controller can be adapted to enable a vacuum source which pneumatically retrieves the packages so as to accomplish step (d), and optionally steps (e) and (g) as well. An optional step is (h) removing the destination cartridge. Steps (a) and (h) can be performed through a single point of access. In a preferred embodiment of the method, the injection system is sealed with the package therein from step (e).

An additional aspect of the invention relates to a sterilization system. This system includes a delivery system configured to receive a plurality of packages containing a solid material which releases gas or vapor when heated, a sterilization chamber that is configured to receive articles to be sterilized, an injector that receives at least one of the plurality of packages from the delivery system, wherein the injector heats the solid material so as to produce gas or vapor therefrom and then guides the gas or vapor into the sterilization chamber, a controller that induces the delivery system to provide a package to the injector and induce the injector to produce the gas or vapor during a sterilization sequence. Advantageously, the gas or vapor can be hydrogen peroxide when the solid material is a complex of hydrogen peroxide. The system can be configured to receive a cartridge containing the plurality of packages. A first delivery member can be provided that has one or more apertures that are configured to receive a source cartridge containing a plurality of packages and are also configured to receive a destination cartridge wherein used packages will be positioned therein following a sterilization sequence. In a preferred embodiment, the first delivery member is comprised of an upper carousel. The delivery system also preferably includes a second delivery member that has at least one aperture that is configured to receive a package from the cartridge and wherein the second delivery member is movable so that the package can be positioned in an opening in the injector by the second delivery member. The second delivery member is preferably comprised of a lower carousel. In one embodiment, the packages are comprised of a package having a solid hydrogen peroxide component encapsulated within an enclosure that has an impermeable film and a gas permeable surface, wherein the gas permeable surface permits gaseous hydrogen peroxide to vent from the package when the package is heated by the heat source. In a preferred embodiment, the impermeable film is a conductive foil, which preferably has a reflective outer surface. The impermeable film can be configured to reflect radiant heat until a heat source is positioned in contact with the reflective surface. A preferred injector for use in the system includes a housing that defines a first chamber, a heat source, and a carriage that is attached to the heat source and is movable between a first position and a second position wherein the heat source is in contact with the package when the carriage is in the second position. The one or more communication passageways can interconnect the first chamber and the sterilization chamber and the carriage configured so that when the carriage is in the second position, the passageways provide a pathway for gaseous hydrogen peroxide to flow from the first chamber into the sterilization chamber. The injector can include a second chamber that functions as a bellows chamber that is at the same or lower pressure than the first chamber when the carriage is in the first position and wherein the first chamber is brought to a lower pressure than the bellows chamber so as to induce the carriage to move towards the package.

An additional aspect of the invention relates to a sterilization system that provides a sterilizing gas to a sterilizing chamber. This system includes a delivery system that receives a plurality of solid sterilization fuel components, an injector that receives one of the plurality of solid sterilization fuel components and induces the component to produce the sterilization gas and further induces the sterilization gas to enter the sterilization chamber, and a control system that induces the delivery system to automatically deliver one of the solid sterilization fuel components to the injector and further induces the injector to produce the sterilization gas from the solid sterilization fuel component. The solid sterilization fuel component preferably produces non-aqueous vapor that can sterilize objects positioned within the sterilization chamber. Thus, the solid sterilization fuel can be comprised of a solid hydrogen peroxide complex that is induced to produce hydrogen peroxide gas in the injector. Optionally, the system can include a source of ultraviolet radiation or plasma. The injector for use in the system can include a housing that defines a first chamber, a heat source, and a carriage that is attached to the heat source and is movable between a first position and a second position wherein heat source is in contact with the solid fuel component when the carriage is in the second position. The one or more communication passageways can interconnect the first chamber and the sterilization chamber and the carriage configured so that when the carriage is in the second position, the passageways provide a pathway for gaseous hydrogen peroxide to flow from the first chamber into the sterilization chamber. The injector can include a second chamber that functions as a bellows chamber that is at the same or lower pressure than the first chamber when the carriage is in the first position and wherein the first chamber is at a lower pressure than the bellows chamber so as to induce the carriage to move towards the package. The delivery system can also be configured to receive a cartridge containing the plurality of packages. Thus, the delivery system can include an upper carousel that has one or more apertures that are configured to receive a source cartridge containing a plurality of packages and are also configured to receive a destination cartridge wherein used packages will be positioned therein following a sterilization sequence. The system can also be provided with a lower carousel that has at least one aperture that is configured to receive a package from the cartridge and wherein the lower carousel is movable so that the package can be positioned in an opening in the injector by the lower carousel. Preferably, the packages are comprised of a package having a solid hydrogen peroxide component encapsulated within an enclosure that has an impermeable film and a gas permeable surface, wherein the impermeable film is configured to reflect radiant heat until a heat source is positioned in contact with the reflective surface and wherein said gas permeable surface permits gaseous hydrogen peroxide to vent from said package when said package is heated by said heat source.

One additional aspect of the invention relates to a method of sterilizing a plurality of objects positioned within a sterilization chamber. This method includes positioning one of a plurality of solid sterilization fuel components within an injector, inducing the one of the plurality of solid sterilization fuel component to produce a non-aqueous sterilization gas, and inducing the non-aqueous sterilization gas to flow from the injector into the sterilization chamber to sterilize the articles contained therein. The sterilization gas is preferably hydrogen peroxide. In one embodiment of the method the articles are also exposed to plasma or ultraviolet irradiation.

BRIEF DESCRIPTION OF THE DRAWINGS

FIG. 2A is a schematic exploded view of a first embodiment of a disk-shaped container including a solid material which releases vapor or gas between a permeable membrane and a conductive foil;

FIG. 2B is a schematic exploded view of a second embodiment of the disk-shaped container which incorporates a screen material;

FIGS. 9A–9E are cross-sectional views schematically depicting the operation of the injector shown in FIG. 8.

DETAILED DESCRIPTION OF THE PREFERRED EMBODIMENT

Reference will now be made to the drawings wherein like numerals refer to like parts throughout. As an improvement to conventional liquid hydrogen peroxide ($H_2O_2$) injection/delivery techniques, the preferred embodiment discloses a unique sterilization system using one or more solid hydrogen peroxide complex sterilization injectors incorporated with a disk delivery system.

Figure 1A:
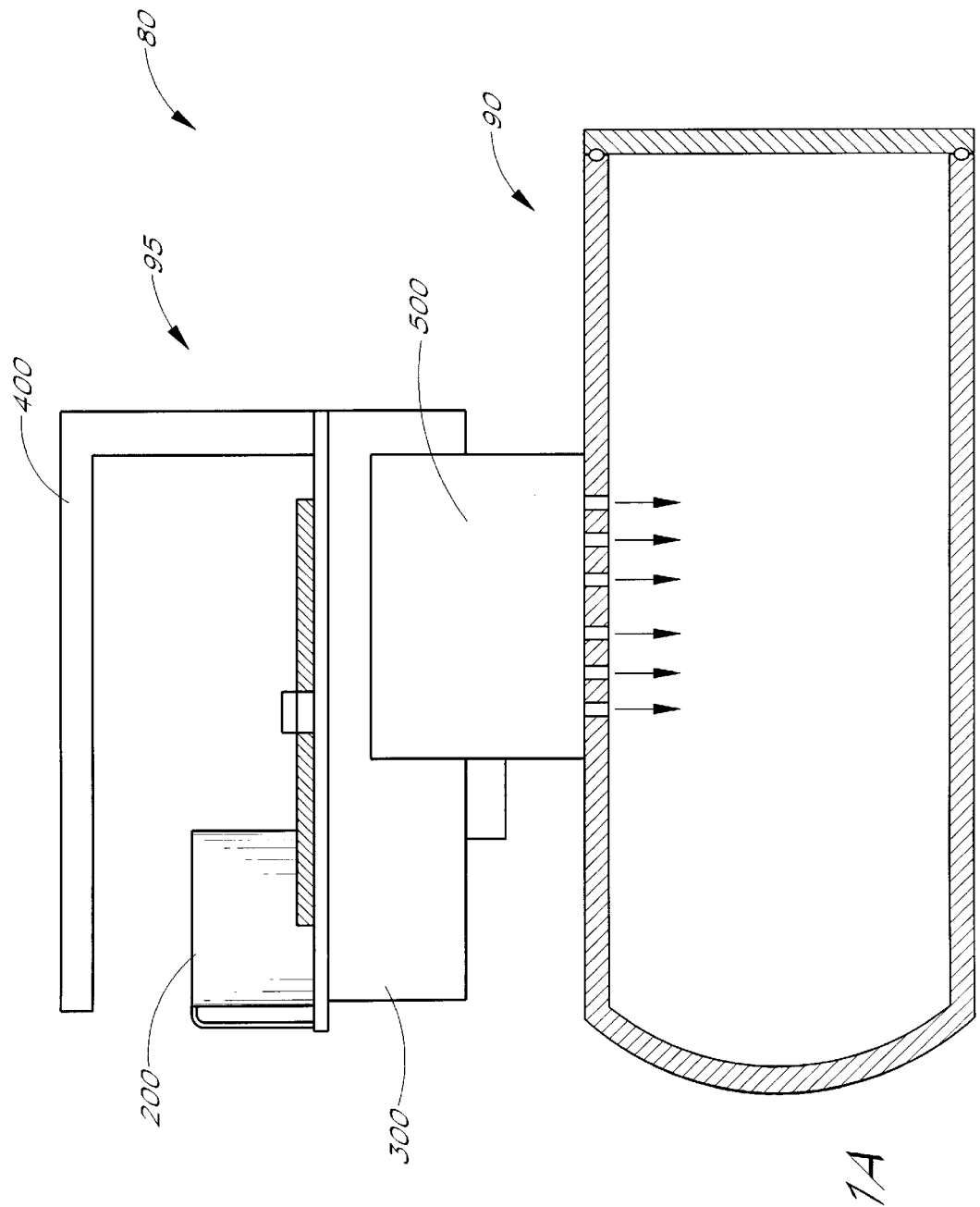
FIG. 1A is a schematic of a sterilization chamber equipped with the injection system of the present invention.
Figure 1B:
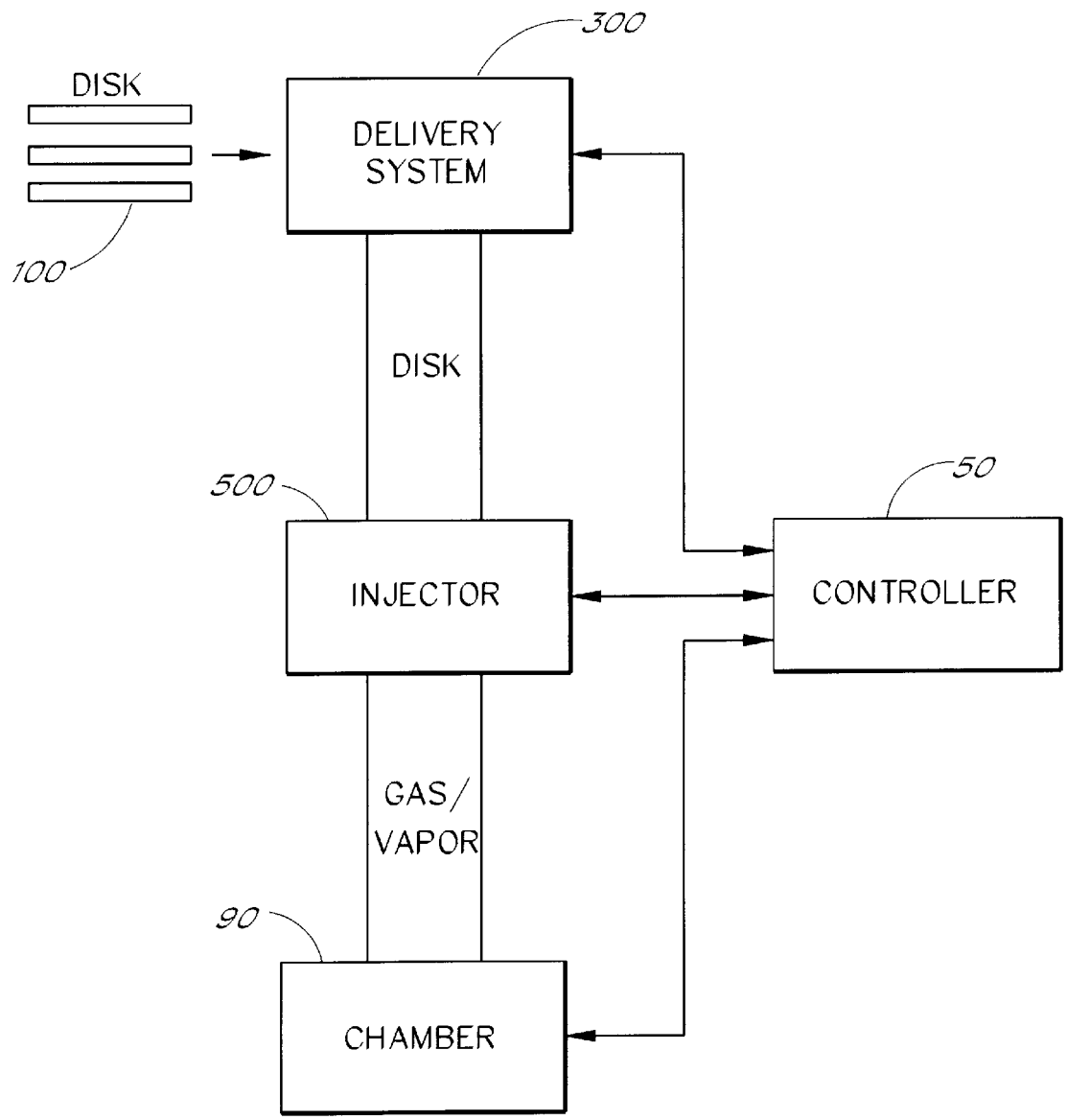
FIG. 1B is a block diagram representing the control system of the present invention.
Figure 2C:
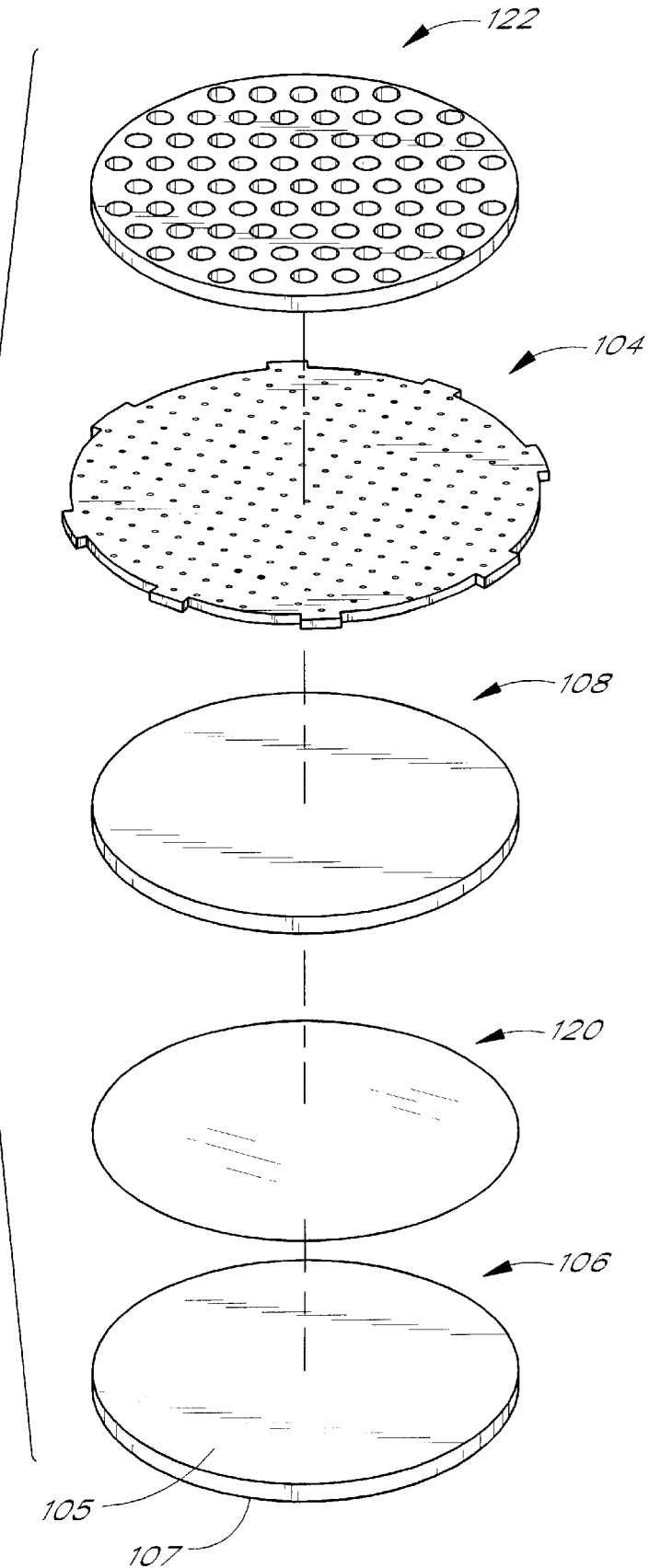
FIG. 2C is a schematic exploded view of a third embodiment of the disk-shaped container which incorporates another gas permeable material and an adhesive layer.

FIG. 1A is a schematic illustration of an exemplary sterilization system 80 including a sterilization chamber 90 equipped with a solid $H_2O_2$ complex sterilization injection system 95. As shown in FIG. 1A, the schematic hydrogen peroxide injection system 95 of the present invention comprises mainly an injector 500 to create and to inject $H_2O_2$ vapor into a sterilization chamber 90 which contains items to be sterilized, and a delivery system 300 assembled to deliver containers containing solid $H_2O_2$ complex into the injector. As indicated in the block diagram of FIG. 1B, the delivery system 300 and the injector 500 are all under the control of a controller 50. The controller 50 is a typical industrial controller that receives signals from sensors within the delivery system 300 and the injector 500 and provides control signals to control the operation of these components as will be described hereinbelow. Further, the controller 50 also receives signals from the sterilization chamber 90 indicative of the status of a sterilization process. As will be appreciated from the following description, the system 80 of the preferred embodiment automatically sterilizes components within the sterilization chamber 90 in an efficient manner. Further, as will be further explained in detail hereinbelow, containers containing solid hydrogen peroxide complex (which will be referred to as peroxide containers) may be loaded onto the sterilization injection system 95 in a cartridge 200 which is configured to hold a number of peroxide containers. Once a cartridge 200 is loaded, the delivery system 300 automatically transfers peroxide containers 100 (FIGS. 2A–2E) into the injector 500. The injector 500 then injects the gaseous content of the container into the sterilization chamber 90 in a manner that will be described hereinbelow. A used peroxide container 100 is, in turn, disposed into a second cartridge (not shown) which holds used peroxide containers 100. This above described cycle continues until the last peroxide container 100 is used and disposed into the used container cartridge. Consequently, the system 80 allows the operator to load a plurality of cartridges 200 into the delivery system wherein each cartridge 200 has a plurality of peroxide containers 100. These containers are then delivered to the injector 500 as needed to perform sterilization or disinfection of the articles which may be placed into the sterilization chamber 90. It will be appreciated from the following discussion that the system 80 is efficient to operate due to the ability to load many peroxide containers 100 at one time and then automatically feed them into the injector 500 as needed as opposed to loading one peroxide container 100 at a time. The peroxide container 100 to be utilized in the present invention can be manufactured by facilitating various materials and methods. FIG. 2A shows, in exploded view, a disk shaped container 100 for holding the solid peroxide complex that is utilized in the system 80. In the first embodiment, the container 100 preferably includes a piece of metallic foil 106, preferably an aluminum foil, a solid material 108 and a gas permeable material 104. As shown in cross-section in FIG. 2D, the metallic foil 106 forms the bottom layer of the disk-shaped container 100, and defines a first surface 105 and a second surface 107. A presently anticipated preferred solid material is a hydrogen peroxide complex which releases hydrogen peroxide gas upon heating. However, a hydrate complex or an ammonia complex may also be used for the same purposes. In this embodiment, the solid peroxide complex 108 is directly placed on the first surface 105 of the aluminum foil 106. In accordance with the principles of the present invention, the second surface of the aluminum foil 106 preferably comprises a reflective surface which is able to reflect the radiation from a heated object away. In this respect, this second surface 107 minimizes heating of the content of the disk shaped container until contact is made with a heated surface and improves thermal conductivity after contact is made. In the present invention, the solid peroxide complex 108 may be in the form of powder, tablets or a dry slurry i.e., a dry paste. The solid peroxide complex 108 is then covered with a gas permeable membrane 104 which defines the top layer of the disk shaped container 100. This gas permeable membrane 104 may be made of a glass filter or material which is also liquid impermeable, such as medical grade TYVEK™ or SPUNGUARD™ materials, so that the hydrogen peroxide gas released from the complex 108 in response to heating by the injector system 500 in the manner described hereinbelow passes through the permeable membrane 104 before diffusing into the chamber 90.

FIG. 2B shows a second embodiment of the disk-shaped container. In this embodiment, in order to provide an even distribution and even heating of all of the solid peroxide complex 108, a screen material 110, such as a metallic or a polymer screen, is pressed over the peroxide complex 108 so that the peroxide complex 108 is evenly distributed into the meshed structure of the screen material 110 in the manner shown in FIG. 2B. The solid peroxide complex 108 may be in the form of a slurry (dried slurry) or powder. If the powder form of the solid hydrogen peroxide complex is to be used, the powder could be slightly wetted with hydrogen peroxide solution (e.g., 30%) and then dried inside the meshed structure to form a dried slurry so that a better adherence to the screen 110 can be provided. In this respect, both the screen material 110 and the solid peroxide complex 108 are again sandwiched between the aluminum foil 106 and the gas permeable membrane 104, as is explained in the first embodiment. The screen material 110 also provides an advantageous mechanical support for the disk shaped container 100 during various processing and transportation steps. The melting temperature of the screen material 110 should be higher than the gas release temperature of the hydrogen peroxide complex 108. The hydrogen peroxide gas release occurs at a temperature range of 20° to 300° C., more preferably 25° to 250° C. In this embodiment, as an alternative to the screen material 110, the aluminum foil 106 can be configured to have a plurality of pockets on the first surface 105 of the aluminum foil 106 to retain the solid peroxide complex 108 in these pockets. These pockets can be formed on the aluminum foil 106 as an array of square or hexagonal cavities using techniques well-known in the art, such as embossing the aluminum foil 106.

FIG. 2C also shows a third embodiment for the disk-shaped container 100. In this embodiment, preferably a layer of adhesive 120, preferably a high temperature adhesive, may be placed over the first surface 105 of the aluminum foil 106. Adhesives 120 on the aluminum foil 106 may, for example, include, but are not limited to, an acrylic or a silicon based high temperature adhesives. Once the high temperature adhesive (will be referred to as adhesive) is applied to the first surface 105 of the aluminum foil 106, the solid peroxide complex 108 is disposed over the adhesive layer 120 in the manner shown in FIG. 2C. The solid peroxide complex 108 is then covered with the gas permeable membrane 104 as in the first and second embodiments. The gas permeable membrane 104 can also be covered with an optional layer of another gas permeable material, such as an inflexible material 122, to mechanically reinforce the underlying flexible membrane 104, or a flexible material to protect the gas permeable membrane 104. In this respect, the inflexible material 122 may be a thin perforated layer of a rigid material such as a layer of aluminum or a rigid polymer. The flexible material could be a thin, perforated metal foil. It is understood that, in this embodiment, the peroxide complex 108 can be held by the adhesive layer 120. The peroxide complex is preferably in the form of powder or dried slurry, as discussed above in connection with the use of a screen material 110. As in the case of the screen material 110, the adhesive layer 120 evenly distributes the solid peroxide complex 108 over the aluminum foil 106 and bonds the individual solid particles to the underlying aluminum foil 106. The use of adhesive layer 120 provides a significantly uniform layer of solid hydrogen peroxide complex 108 over the aluminum foil 106 which, in turn, provides an even heating of the peroxide complex 108 during the process.

Although these three embodiments are the preferred embodiments to construct the solid peroxide complex containers 100, it is understood by those skilled in the art, that the peroxide containers 100 can also be manufactured in numerous alternative ways. For example, in the first embodiment, the adhesive layer 120 or the embossment can be applied over the first surface 105 of the aluminum foil 106. Similarly, in the third embodiment the adhesive layer 120 can be replaced by an embossed aluminum layer to evenly distribute and to retain the solid peroxide complex 108 over the aluminum foil 106. Further, in the second embodiment, the adhesive layer 120 and the screen material 110 can be used together to provide a better distribution for the peroxide complex 108. In this alternative embodiment, the adhesive layer 120 can initially be applied over the first surface 105 of the aluminum foil 106 so that the peroxide complex 108 and the screen 110 can be placed over the adhesive layer 120. This embodiment is particularly useful to prepare peroxide containers 100 comprising a significant amount of peroxide complex 108, if needed. In this case, the combined effect of the screen and the adhesive on the metal foil 106 provides an effective distribution for the excessive peroxide complex 108.

In accordance with the principles of the present invention the adhesive layer 120 can be replaced by other alternative adhesives. Examples of common materials to be used as an adhesive include, but are not limited to, acrylic adhesives such as A10 or A25 (3M brand) or NT100 and NT200AP (Dielectric Polymers brand) and silicon adhesives such as NT1001 (Dielectric Polymers brand). These adhesives can also be advantageously used to form tapes, double coated tapes and transfer tapes to increase the uniformity of the adhesive layer.

Additionally, it is also within the scope of the present invention to use alternative materials to replace aluminum foil 106. This can be done by replacing one side of the gas permeable membrane with an impermeable membrane, made of material such as MYLAR™, PTFE or a polycarbonate film. Preferably, the impermeable film side forms the bottom surface of the container 100 and the upper surface is gas permeable membrane. The use of an impermeable film eliminates the need to use of reflective metallic foils. The metallic foil embodiment is particularly useful in conductive and convective heating, whereas the impermeable film applications are most useful in connection with irradiative heating such as microwave heating, RF heating or Infrared (IR) heating. In fact, It will be particularly advantageous to use disks having permeable layers on both the top and the bottom of the disks for microwave, RF heating or convection heating applications.

Alternative heating sources can be used in conjunction with alternative techniques to prepare hydrogen peroxide complexes. For example, during the preparation process, hydrogen peroxide complex can be mixed with a susceptor material, i.e., a material which can easily absorbs heat and transfers to neighboring material. The susceptor materials absorbs the heat and effectively distributes the heat inside the hydrogen peroxide complex body so that hydrogen peroxide can reach the gas release temperature. Examples of common materials used as a susceptor include, but are not limited to, carbon black, metallic powders and combinations thereof.

Figure 2D:
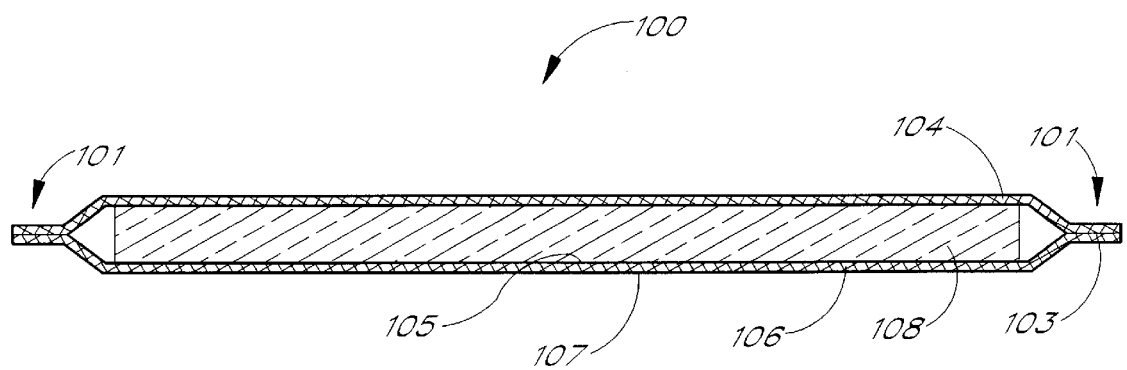
FIG. 2D is a cross-sectional view of the disk-shaped container shown in FIG. 2A.

FIG. 2D shows an exemplary cross-sectional representation of the disk shaped solid peroxide container 100 for the first embodiment. As shown in FIG. 2D, the container 100 can be formed by bonding together the upper gas permeable membrane 104 and the lower aluminum foil 106 along an edge section 101 surrounding the disk container 100 so that the solid peroxide complex 108 is sandwiched between these two layers. Specifically, in order to seal this edge section 101, a suitable adhesive may be applied into the interface 103 between the edges of these layers 104, 106 and the layers are then firmly pressed towards each other. Additionally, a heat seal can be also applied to seal the edge section 101. Although the construction of the disk shaped container 100 is explained for the first embodiment, it is understood by those skilled in the art, that the same principles are also applied to the other embodiments.

Figure 2E:
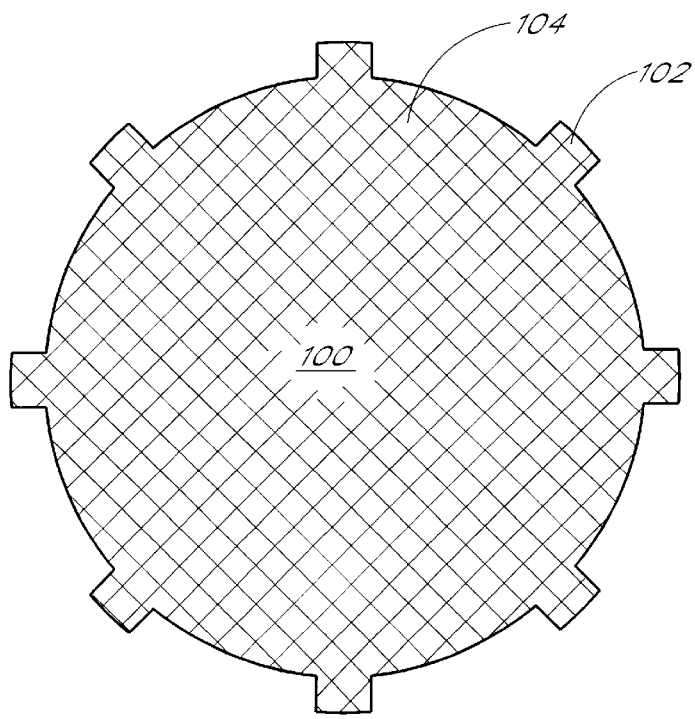
FIG. 2E is a top view of the disk-shaped container shown in FIG. 2A.

As illustrated in the plane view of FIG. 2E, once the edge seal is completed, the edge section 101 is configured along the sealed section 103 to form a plurality of radially distributed tab features 102 along the perimeter of the disk container 100. These tab features 102 enable the disk-shaped container 100 to fit securely into the cartridge 200 and the apertures of the lower carousel of the delivery system 300 as will be described hereinbelow.

Figure 2F:
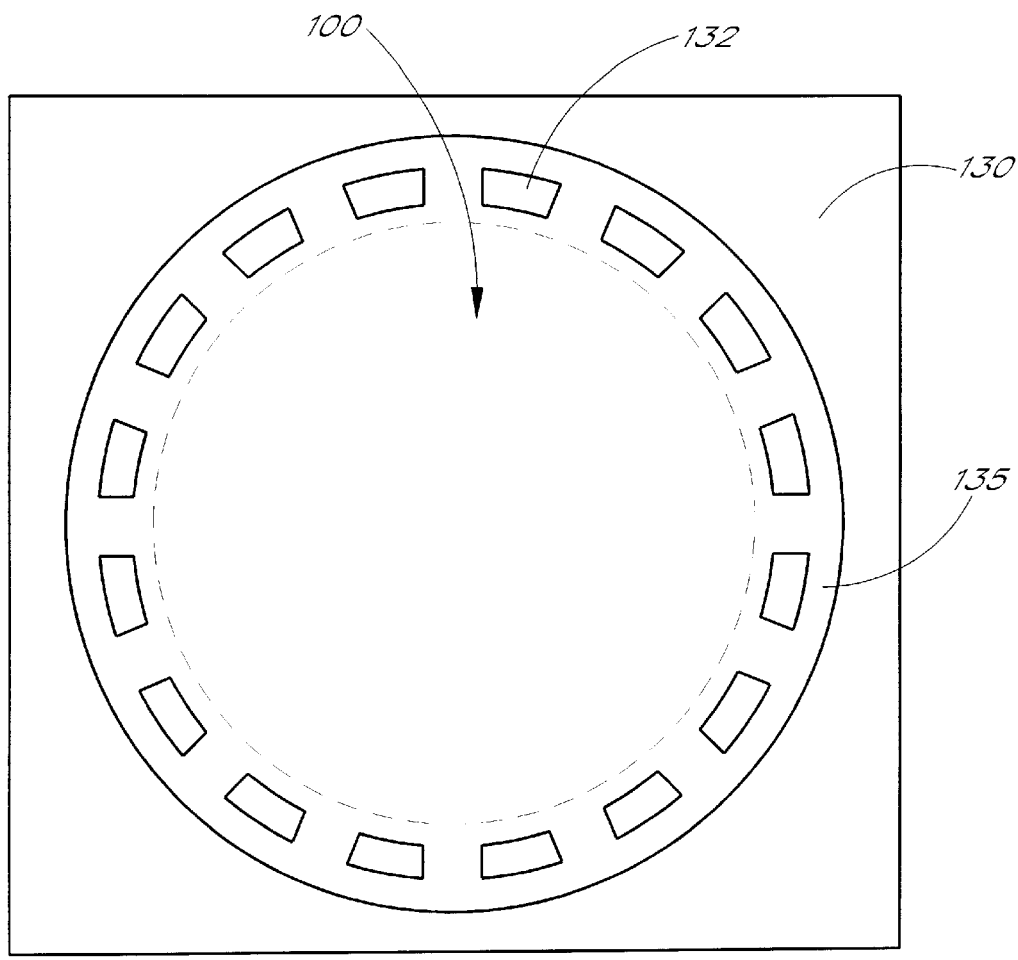
FIG. 2F is a top view of an embodiment of the container incorporated into a supporting material and provided with holes for passage of gas or vapor.
Figure 2G:
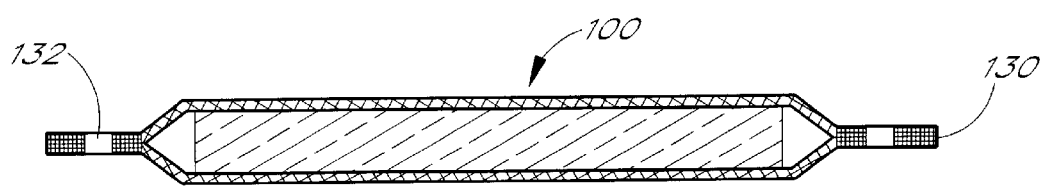
FIG. 2G is a cross-section view of the disk-shaped container shown in FIG. 2F.

FIG. 2F and 2G show an alternative embodiment to configure solid hydrogen peroxide containers 100. In this embodiment, after sealing the edge section of the peroxide disk 100, a layer of supporting material 130 is attached along the perimeter of the disk container 100 as in the manner shown in FIGS. 2F and 2G. This material layer can, for example, be a layer of durable plastic. Once this layer is attached to the peroxide container 100, a number of holes 132, which are positioned on the supporting material and around the perimeter of the disk shaped container 100, is configured as in the manner shown in FIG. 2F. These holes 132 provide a passage for the gases released from the top gas permeable layer 104 or 122 during the process. Thus, the gases can diffuse to the opposite side of the container 100. The support 130 can comprise a sealable surface 135 around the perimeter of the holes 132.

Figure 3A:
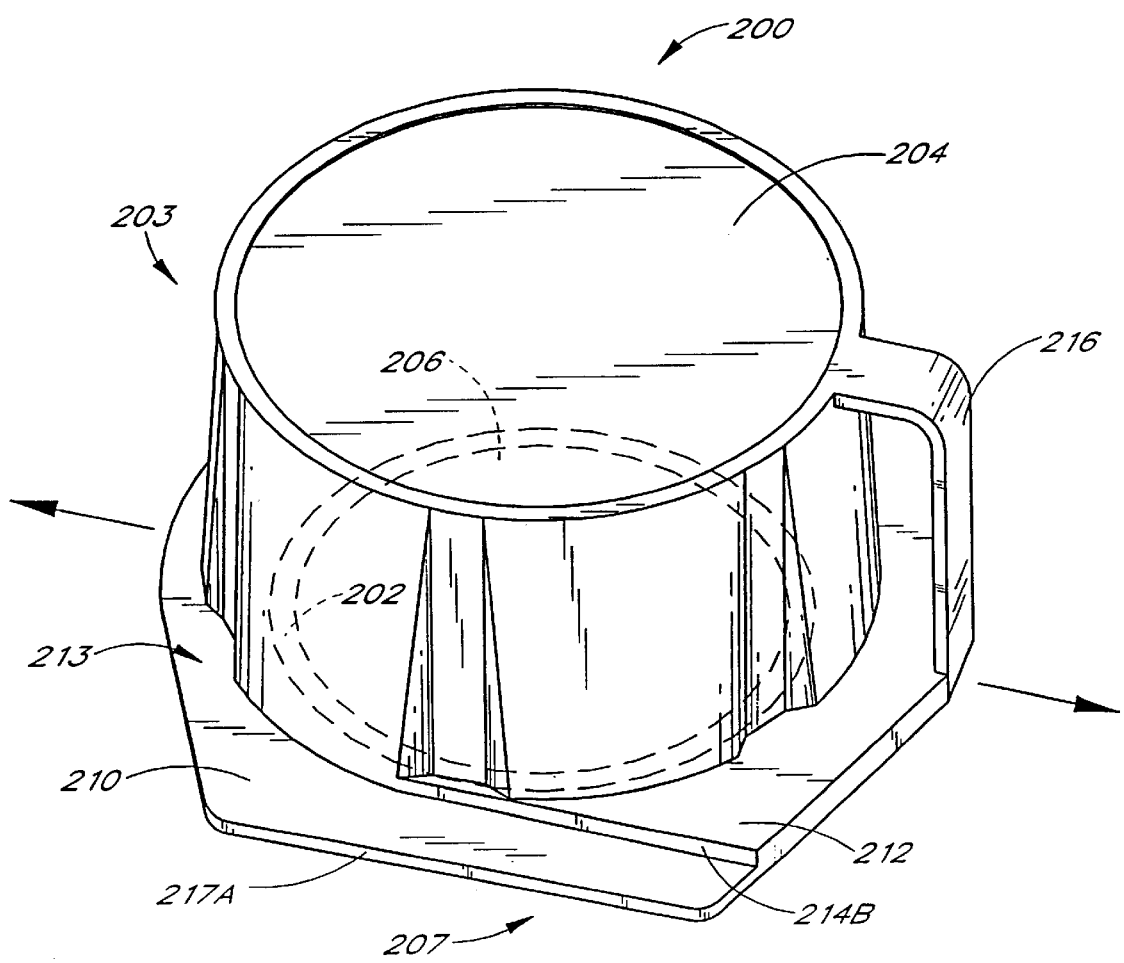
FIG. 3A is a schematic view of a cartridge for holding the disk-shaped containers shown in FIGS. 2A–2E.

FIG. 3A illustrates a cartridge 200 that receives the disk-shaped solid peroxide containers 100 (or peroxide disks) illustrated in FIGS. 2A–2E. The cartridge 200 has a cylindrical body 203 comprising an open lower-end 206 and a covered upper-end 204 portions. As seen in FIG. 3A, the cartridge 200 further comprises a base section 213 extending perpendicularly out of the lower-end 206 peripheral of the hollow cylinder 203 that defines a raised surface 212 positioned adjacent the cylindrical body 203 and a recessed surface 210 positioned at the outer extremity of the base section 213. Further, a handle 216 projects outward from the outer peripheral of the upper-end 204 of the hollow cylinder 203, which bends down perpendicularly towards the base section 213 and into engagement with the correspondingly shaped raised portion 212 of the base section 213.

Figure 3B:
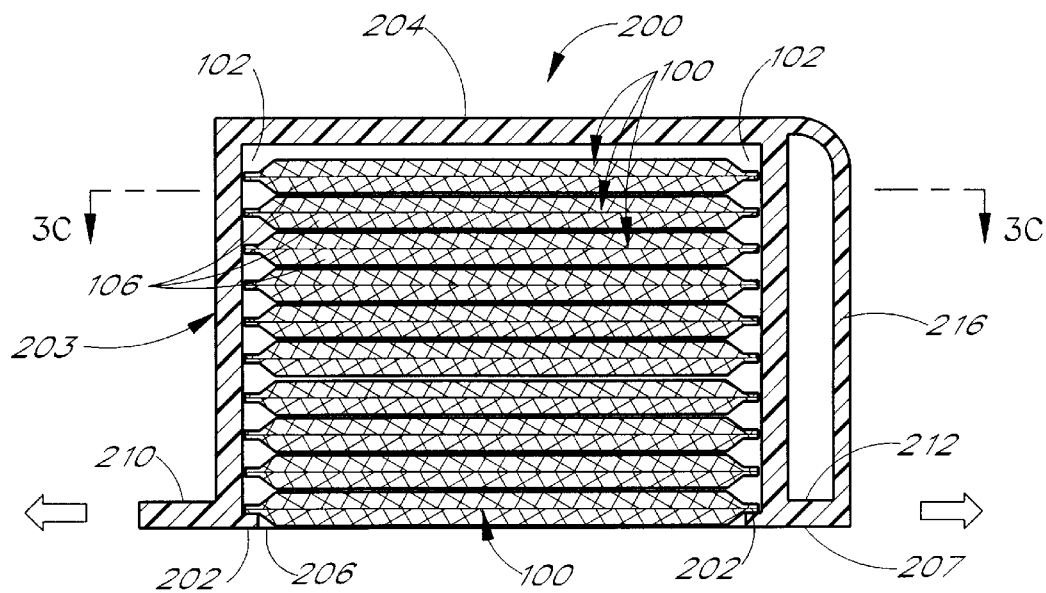
FIG. 3B is a cross-sectional view of the cartridge shown in FIG. 3A wherein the cartridge includes a plurality of disk-shaped containers.
Figure 3C:
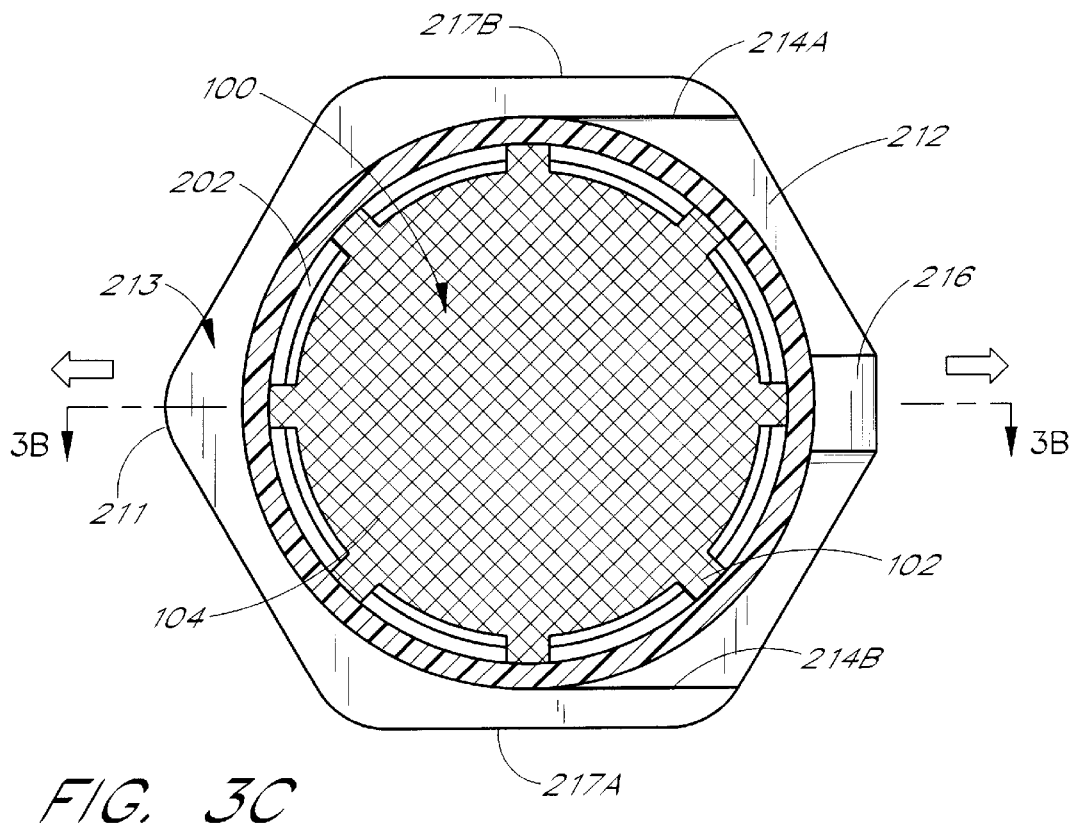
FIG. 3C is a top view of the cartridge shown in FIG. 3A.

As illustrated in detail in FIG. 3B, the cylindrical body 203 further comprises an inner lip section 202 extending inwardly and circumferentially around the lower-end peripheral of the hollow cylinder 203 in the manner shown in FIG. 3B. Referring to FIG. 3B, the bottom surface 207 of the base section 213 of the cartridge 200 is formed so that the plane of the bottom surface 207 defines a flat bottom surface for the cartridge 200 for creating a seal thereto. FIG. 3C shows that, in plane view, the base section 213 of the cartridge 200 has a hexagonal shape with rounded corners 211. The recessed portion 210 of the base section surface 213 extends from the side 217a through the opposite side 217b in a counter-clockwise manner and is used to rotationally locate the peroxide container. As shown in FIG. 3C, the walls 214A and 214B of the raised section 212 are formed adjacent the outer surface of the cylinder 203. As will be explained further in the application, the entire recessed portion 210 is dimensioned and configured to engage the cartridge 200 with the upper carousel 220 (FIG. 4) of the delivery system 300.

As can be seen in cross-section in FIG. 3B, a plurality of peroxide disks 100 can be stacked into the cartridge 200. In the preferred embodiment, each cartridge 200 contains ten of the peroxide disks 100. Along their vertical axis, peroxide disks 100 are stacked on top of one another and parallel to the bottom surface 207 of the cartridge 200 so that their aluminum foil 106 faces towards the lower end 206 of the hollow cylinder 203. The diameter of the disk 100 is made slightly smaller than the diameter of the cylinder 203. In this design configuration, the flexible tabs 102 help to secure the disks 100 in the cylinder 203 in the manner shown in FIG. 3C. Hence, by means of the tab features 102, the circumferential edge of the peroxide disks 100 clears the inner surface of the hollow cylinder 203. The tabs 102 are preferably flexible so that peroxide disks 100 can be extracted from the cartridge 200, through the inner lip 202, at the lower end 206 of the hollow cylinder 203 in the manner described hereinbelow.

Although, in the preferred embodiment, the peroxide disks 100 are stacked into cartridges 200, it is also within the scope of the present invention to use other methods to provide these peroxide disks 100 for the system 80. For example, a number of peroxide disks 100 can be joined at their edges in a z-fold fashion and placed into cartridges 200 so that the peroxide disks 100 can be fed in series into the injector 500. Additionally, such joined disks can also be rolled onto a core (or rolled without a core) within the cartridge 200 so that the peroxide disks 100 can be fed in series into the injector 500.

Figure 4:
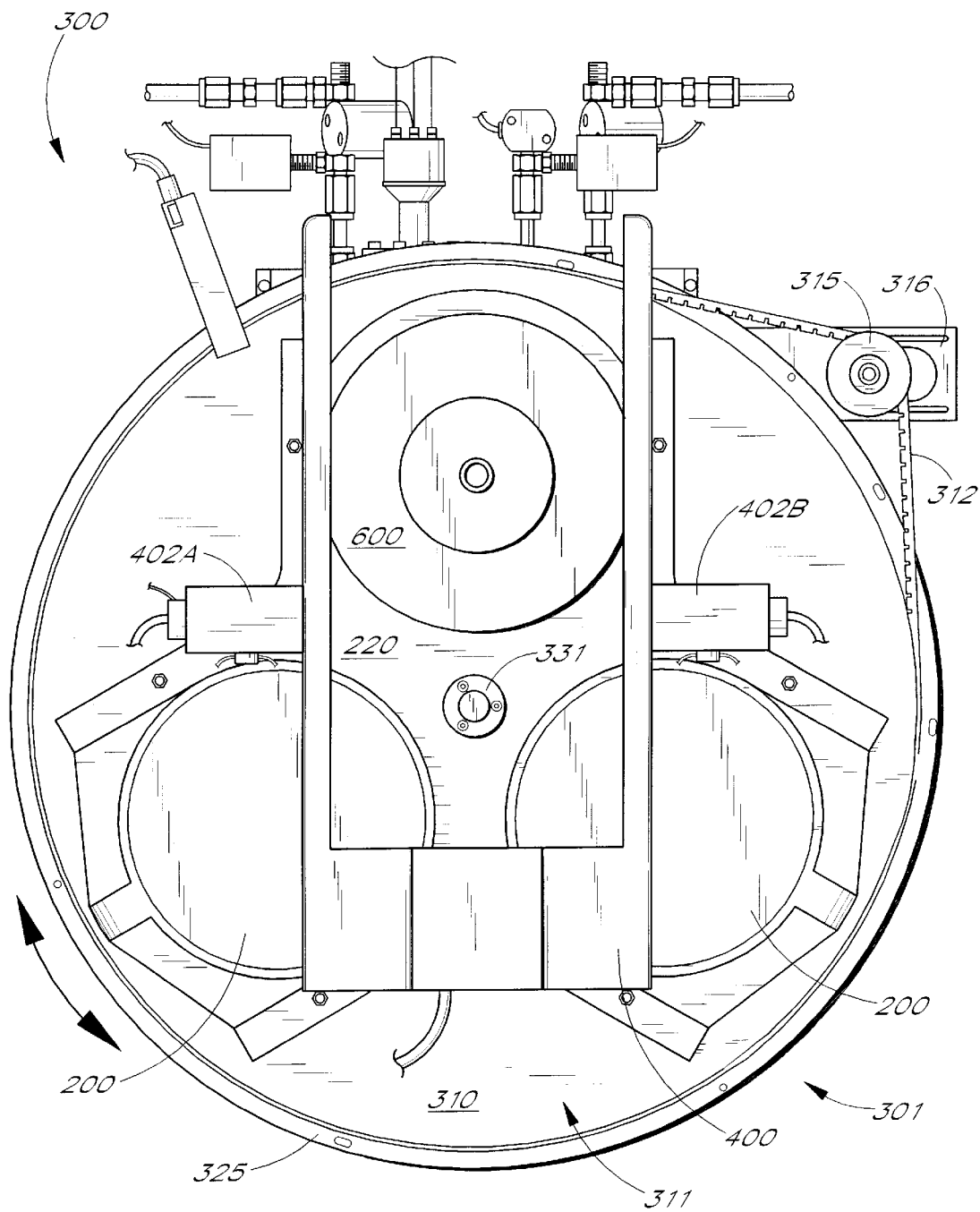
FIG. 4 is a top view of the sterilization delivery system.
Figure 5:
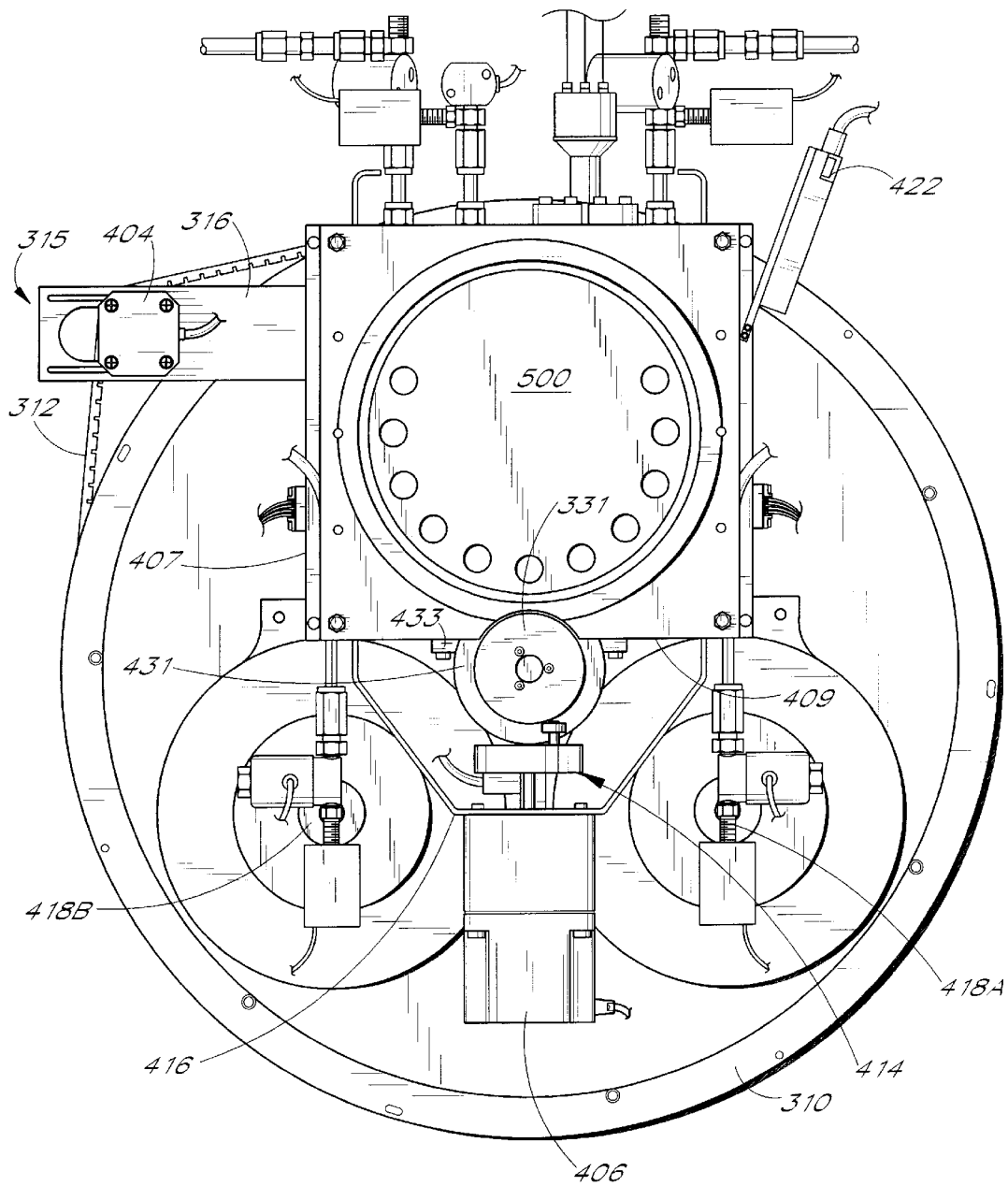
FIG. 5 is a bottom view of the sterilization delivery system shown in FIG. 4.

A sterilant delivery assembly 301 of the delivery system 300 is shown in top view in FIG. 4 and in bottom view in FIG. 5. This assembly 301 is positioned immediately above the injector 500 so as to be able to provide and remove peroxide disks to and from the injector 500. As shown in FIG. 4, the delivery assembly 301 is designed for handling and delivering the peroxide disks 100 to the injector 500 via the cartridge 200 as well as removing used disks from the injector 500. As explained in detail hereinbelow, the delivery assembly 301 is rotatable about a z-axis that is perpendicular to the plane of the paper in FIGS. 4 and 5 and movable along the z-axis to change the relative elevation of the delivery assembly 301. Further, the delivery assembly 301 includes a first delivery member 220 and a second delivery member 310 which are mounted on a drive shaft 331, and are movable independently along and about the z-axis to handle and transport peroxide disks 100 to and from the cartridges 200 and the other process stations of the system 80 including the injector 500. Since the delivery assembly 301 is rotatable about the z-axis, as explained more fully below, the first and the second delivery members 220, 310 will sweep a generally circular area. In general, all work stations or source and destination cartridges are positioned within the ambit of the swept area so that the delivery members 220, 310 can efficiently handle and deliver the peroxide disks 100.

As shown in the top view in FIG. 4, the first and the second delivery members 220, 310 are mounted at their mid-point atop a drive shaft 331. Further, the second delivery member 310 is circular in shape and includes a peripheral guide rail 325 formed on the upper surface 311 of the second delivery member 310. The guide rail 325 is configured to receive a flexible drive belt 312 that is engaged with the guide rail 325 so that movement of the belt 312 results in rotation of the second delivery member 310 between its initial and extended positions. The belt 312 is also engaged with a drive pulley 315 mounted on a pulley support brace 316 positioned adjacent the assembly 301.

As shown in the bottom view of FIG. 5, the drive pulley 315 is connected to a first bi-directional drive motor 404 which is secured by the pulley support brace 316 that is mounted over a side wall 407 of the injector unit 500. Rotation of the drive pulley 315 in one direction or the other will cause a corresponding rotational motion of the delivery assembly 301 about the drive shaft 331. The delivery members 220, 310 can be selectively raised and lowered from their home positions by a mechanical drive train 414, shown in FIG. 5, under the control of the controller 50 (FIG. 1B) in the manner described more fully hereinbelow. The drive shaft 331 of the delivery assembly 301 is connected to and controlled by a second bi-directional drive motor 406 through the mechanical drive train 414 which extends between and interconnects the drive shaft and the drive motor 406. The drive shaft 331 housing 431 is positioned in a secured manner against a side wall 409 of the injector 500 via bolts 433. In the preferred embodiment, the drive motor 406 for the drive shaft 331 facilitates movement of the drive shaft 331 without requiring the drive trains 414 and the motor 406 to be located on the z-axis. In fact, this off-set or cantilevered configuration of the driving system leads to a compact arrangement. In particular, the second drive motor 406 is mounted on a trapezoid shaped brace 416 which is, in turn, mounted on the same wall 409 of the injector 500 as the drive shaft housing 431.

As shown in FIG. 5, the bottom part of the delivery assembly is provided with plurality of vacuum means 418A–418B. The vacuum means can be any of a number of appropriate mechanisms which can pneumatically attach and detach to a surface. In the preferred embodiment, a suction cup is used. The vacuum means 418A–418B are connected to a selectively operated vacuum source (not shown) via appropriate hoses or tubing. The vacuum source can be selectively enabled or inhibited by the controller 50 in a manner well known in the art to pneumatically attach and detach the peroxide disks 100 from their respective positions in the manner that will be described hereinbelow.

Figure 6A:
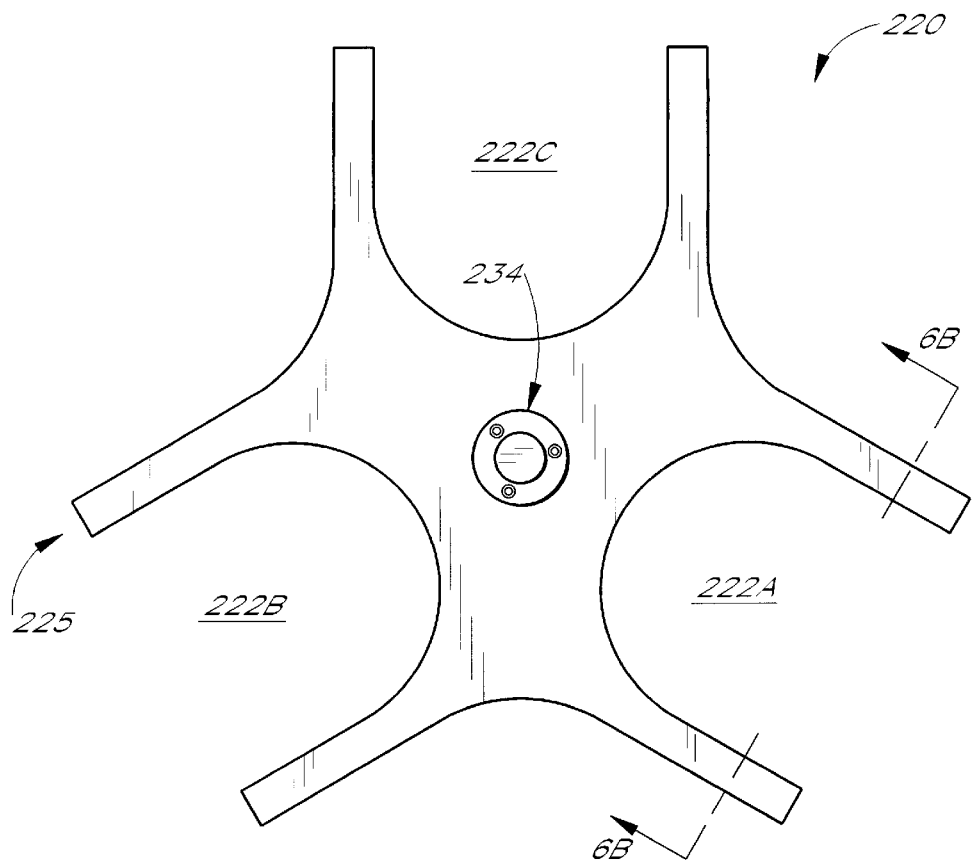
FIG. 6A is a schematic view of the first delivery member.

As illustrated in FIG. 6A, the first delivery member 220 is comprised of an upper carousel in this embodiment which has a plurality of receiving ports 222A–222C that are configured to accommodate various articles such as cartridges 200 and/or an injector lid 600 as described below. In particular, in the preferred embodiment, the upper carousel 220 includes three "U" shaped receiving ports 222A–222C which are positioned 120 degrees apart from each other about the carousel 220 which is attached to the drive shaft 331 at a center point 234. The upper carousel 220 is preferably constructed from a metal such as aluminum or durable polymer, or the like.

Figure 6B:
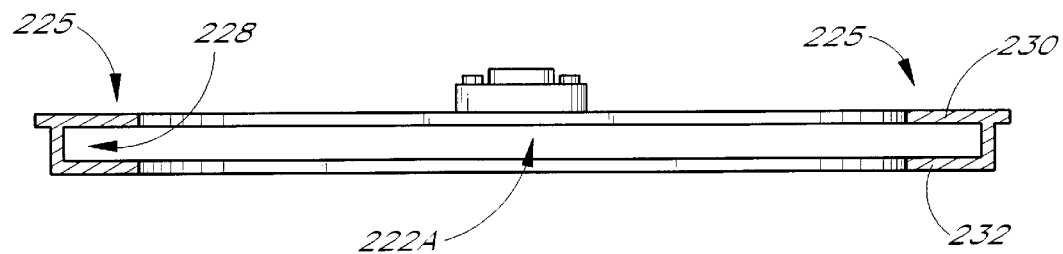
FIG. 6B is a detailed cross-sectional view of a portion of the first delivery member shown in FIG. 6A.
Figure 6C:
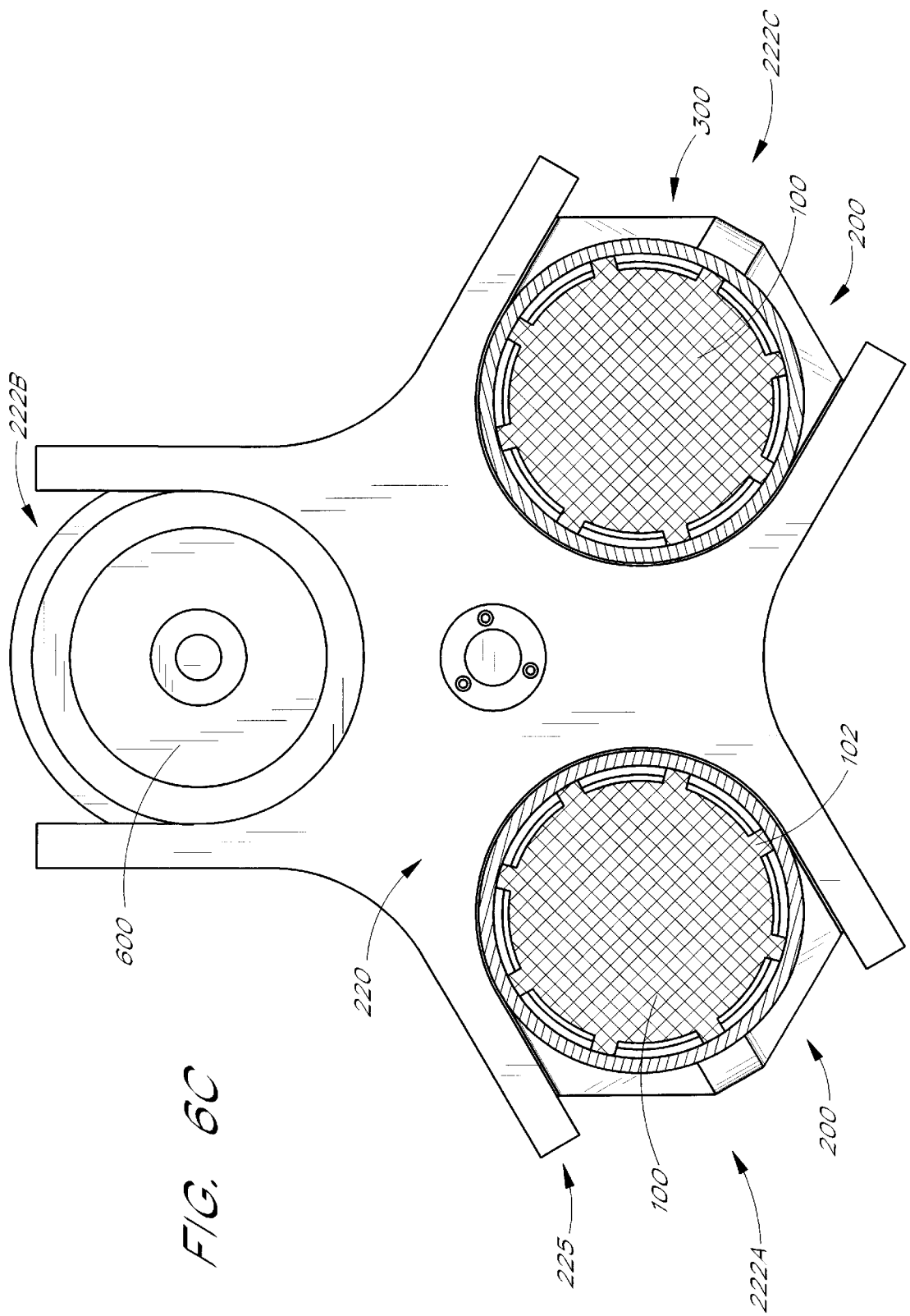
FIG. 6C is a schematic view of the first delivery member shown in FIG. 6B wherein an injector lid and cartridges are positioned into the receiving ports therein.

As shown in FIG. 6B, the U-shaped ports 222A–222C are further configured to have rectangular "C" shaped tracks 230 which define openings 228 that face each other. The tracks 230 are dimensioned and positioned so that the cartridge 200 and the injector lid 600 (See FIG. 8) can slide in the tracks 225 in FIG. 6C. In particular, the recessed portion 218 fits within tracks 230 to retain the cartridge 200 in the carousel 220.

Figure 7A:
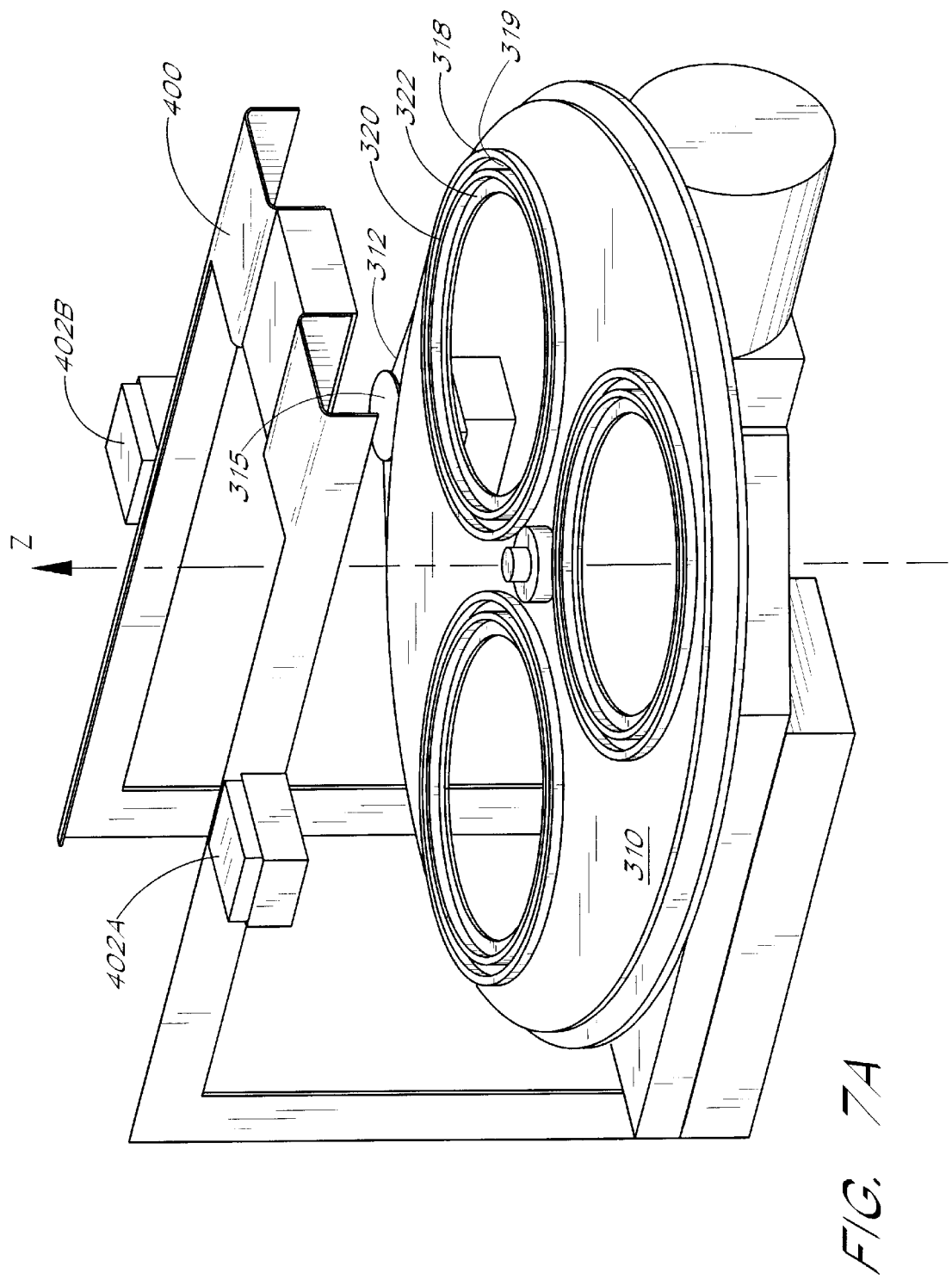
FIG. 7A is a schematic view of the second delivery member.
Figure 7B:
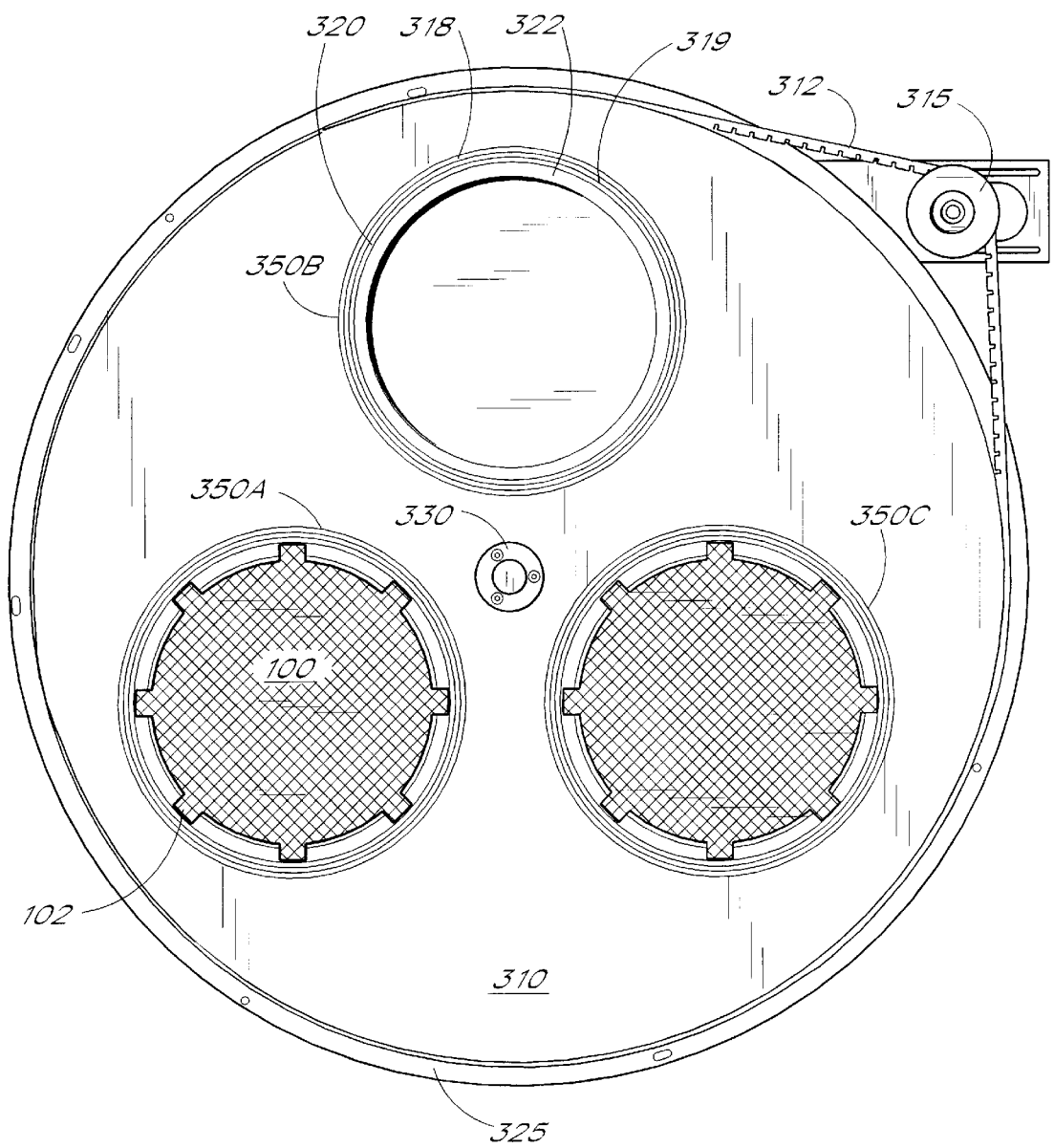
FIG. 7B is a top view of the second delivery member.

The second delivery member 310 will now be described in reference to FIGS. 7A and 7B wherein the first delivery member 220 has been removed for clarity. The second delivery member is comprised of a lower carousel 310 having a plurality of apertures to accommodate the peroxide disks 100. In the preferred embodiment, the lower carousel 310 includes three circular apertures 350A–350C which are radially distributed about the z-axis and about the drive shaft mounting hole 330 so that the center points of the circular apertures 350A–350C are positioned 120° apart from each other. Each circular aperture 350 is configured to have a recessed lip section 322 and a pair of raised surfaces 318, 320. The recessed lip section 322 extends inwardly and circumferentially around the aperture 350A–350C such that the lip section is able to hold one peroxide disk 100 by the tab features 102 in the manner shown in FIG. 7B.

The first and second raised surfaces 318, 320 surrounding the apertures 350 both extend outward from the upper surface of the lower carousel 310. The second raised surface 318 is positioned concentrically around the first raised surface 320 which is further positioned concentrically around the aperture 350A–350C. The second raised surface 318 is spaced apart from the first raised surface 320 to define a circular slot 319 between the first and the second raised surfaces 318,320 so that the circular slot 319 can receive an o-ring 321.

Figure 7C:
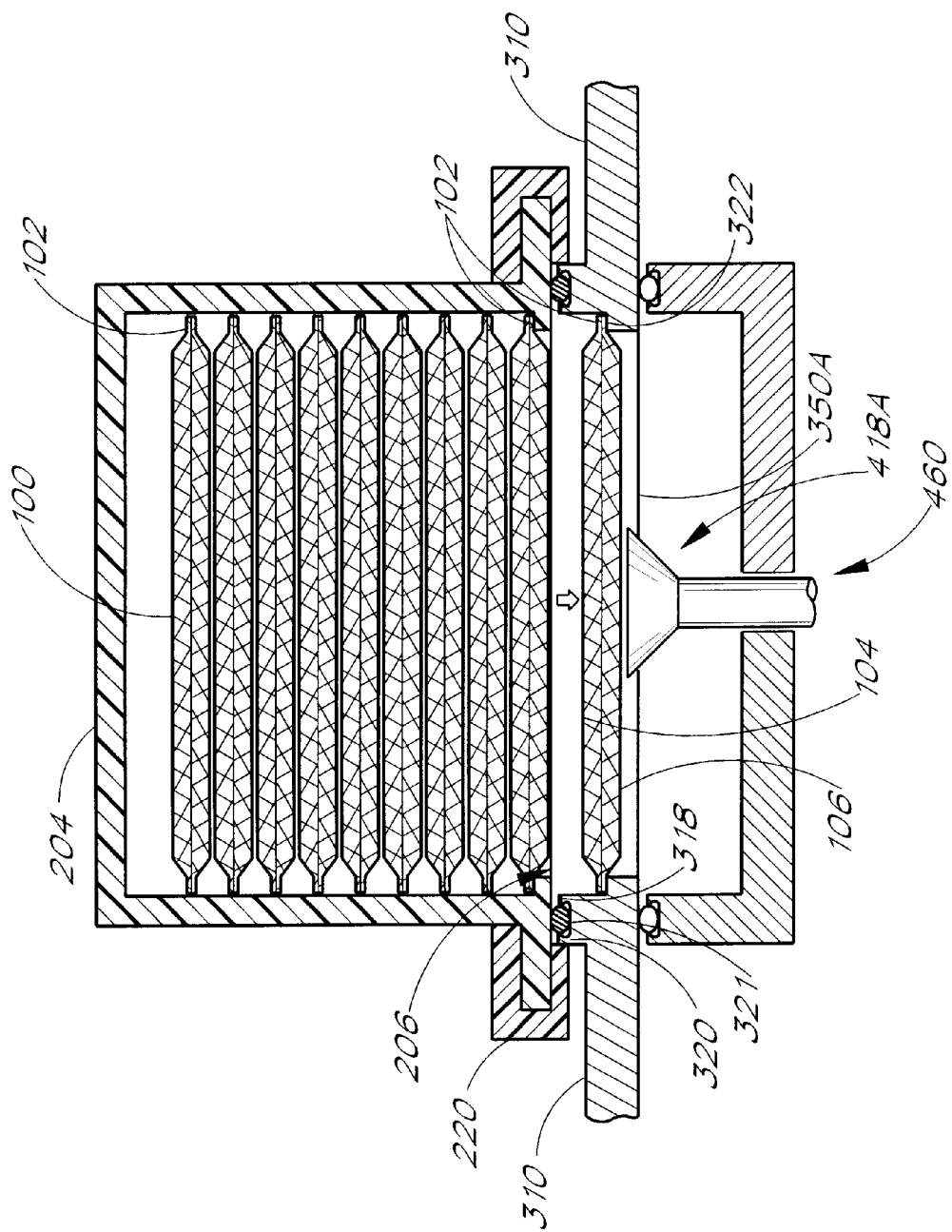
FIG. 7C is a cross-sectional view of an aperture of the second delivery member shown in FIG. 7B wherein the cartridge in the upper carousel receiving port is positioned over the aperture.

FIG. 7C shows schematically the way that the delivery system 301 works and delivers the peroxide disks 100 from the upper carousel 220 to the lower carousel 310. As shown in FIG. 7C, during the operation, the upper carousel 220 is positioned over the lower carousel 310 so that the o-ring 321 between the raised surfaces 318, 320 seals the bottom surface of the cartridge 200 against the raised surfaces 318, 320 of the lower carousel 310. The upper and lower carousels 220, 310 are then moved downward so that the bottom surface of the lower carousel 310 seals the housing 460 of the vacuum means 418A as in the manner shown in FIG. 7C. Once the vacuum is applied through vacuum means 418A, the peroxide disk 100 located above the vacuum means 418A is pulled towards the vacuum means 418A by raising the upper carousel 220 and grabbed by the vacuum means 418A.

One of the vacuum means 418A, described above in reference to FIG. 5, is then configured to extend through the aperture 350A and extracts one peroxide disk 100 from the cartridge 200 in the port 222A and places it into the aperture 350A. In particular, the vacuum means 418A extends through the aperture 350A and induces the peroxide disk 100 to be pulled through the opening 206 in the base 207 of the cartridge 200(See FIG. 3B). As the tabs 102 are somewhat flexible, the tabs 102 deform to allow the disk 100 to be extracted from the cartridge 200 as the upper and lower carousels 220, 310 are raised. The disk 100 is then positioned in the aperture 350A with the tabs 102 engaged with the lip 322 in the manner shown in FIG. 7C.

The operation of the delivery system is controlled by the controller 50. Various externally mounted linear and vertical position sensors and switches 422 (one shown in FIG. 5) provide the information regarding the position of the upper and lower carousels 220 and 310 to the controller 50 which activates various operation steps in the manner that will be described below. The vertical positions of the delivery assembly shaft can also be mechanically read by a cam and cam follower arrangement, through an electrical analog device such as an optical switch or numerous other means well known in the art.

As shown in FIG. 4, the system 80 is also equipped with a bar code reader 402A and bar code burners 402B to provide effective handling and delivery of the peroxide disks 100 in the cartridges 200. The bar code reader 402A reads a bar code on the new cartridges and activates the operation. The bar code burner 402B burns the bar code onto the empty cartridges by means of an Infrared lamp to mark the cartridge with the used disks (destination cartridge). The bar code reader 402A could be an optical sensor mounted on a metal frame 400 which is attached to the delivery system 300 shown in FIG. 4. These and the other aspects of the invention will be more fully explained hereinbelow.

The operation of the delivery system 300 is as follows:

The system 300 is initialized by the controller 50 rotating the upper carousel 220 60° counterclockwise from the home position shown in FIG. 4. As shown above in the FIG. 6C, a source cartridge 200 containing multiple new peroxide disks 100 are inserted manually into upper carousel port 222A after removing any used cartridge in the upper carousel 220. The upper carousel 220 and the lower carousel 310 are rotated by the controller to receive a destination cartridge 200 at the port 222C. As discussed above, each cartridge contains a bar code which is read by the bar code reader 402A so that the controller 50 is aware that the delivery system 300 is loaded with a new cartridge. Then, the controller 50 induces the optical heat source 402B to burn the bar code on the empty destination cartridge 200 in the port 222A of the upper carousel 220.

The controller then induces the upper carousel 220 to rotate 60° clockwise to its home position (FIG. 4) to align the source cartridge 200 in the port 222A of the upper carousel 220 with the aperture 350A in the lower carousel 310. At this point the delivery assembly 301 is engaged and moves downward along the shaft 331 to a position adjacent the injector 500. This position is verified by a position sensor so that the controller 50 preferably receives a signal indicative of the position of the lower carousel.

Once the lower carousel is in the lowered position, the first peroxide disk 100 is pulled out of the source cartridge 200 in the port 222A at the upper carousel 220 by the vacuum means 418A located under the aperture 350A in the manner shown and described in reference to FIG. 7C.

The delivery assembly 301 moves upward while the upper carousel 220 and the lower carousel 310 are disengaged.

Further, once the peroxide disk 100 is placed into the aperture 350A in the lower carousel 310, the vacuum is released thereby positioning the disk 100 in the aperture 350A.

The lower carousel 310 is rotated 120° clockwise over an opening 602 in the injector 500 (See FIG. 8) so that the peroxide disk is placed over the injector opening 602. This movement of the lower carousel 310 preferably positions the new disk 100 above the injector opening 602 and immediately underneath a perforated plate 605. The perforated plate is positioned under an injector lid 600 via bolts 613 in a manner shown in FIG. 8.

The controller 50 then induces the lower carousel 310 and the upper carousel 220 to move together to engage so that the injector lid 600 is positioned over the disk 100 captured in the lower carousel 310 and positioned over the opening 602 in the injector housing 601. The delivery assembly 301 is then moved downward so that the disk 100 is positioned over the opening 602 of the injector 500 with the lid 600 positioned thereon creating a seal. The injector 500 then performs the injection process that will be described in reference to FIGS. 8 and 9 hereinbelow wherein the disk content 108 is heated to produce the peroxide gas.

Subsequently, the delivery assembly 301 then moves upward so as to remove the used disk 100 from the injector 500. During the upward motion, the upper carousel 220 and the lower carousel 310 are disengaged. The lower carousel 310 is then rotated 120° and placed under the destination cartridge. At this point, the used peroxide disk is pushed into the destination cartridge 200 by the vacuum means 418B and by the downward motion of the upper and lower carousels 220, 310.

The process is then repeated but in the opposite rotational direction. When the destination cartridge is filled with used disks, the destination cartridge is rotated 60° clockwise and replaced with a full source cartridge for another cycle.

Figure 8:
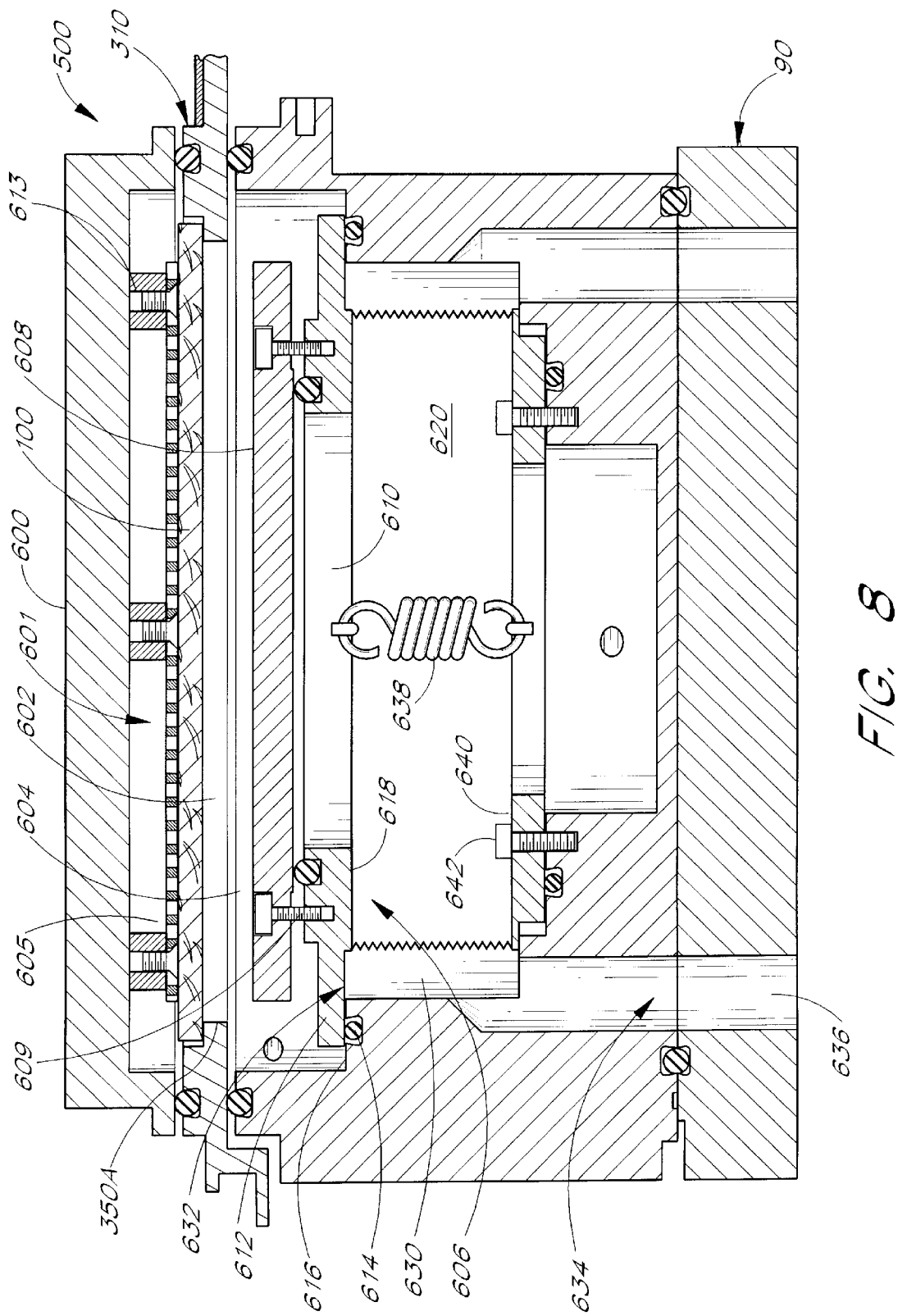
FIG. 8 is a cross-sectional view of the injector.
Figure 9B:
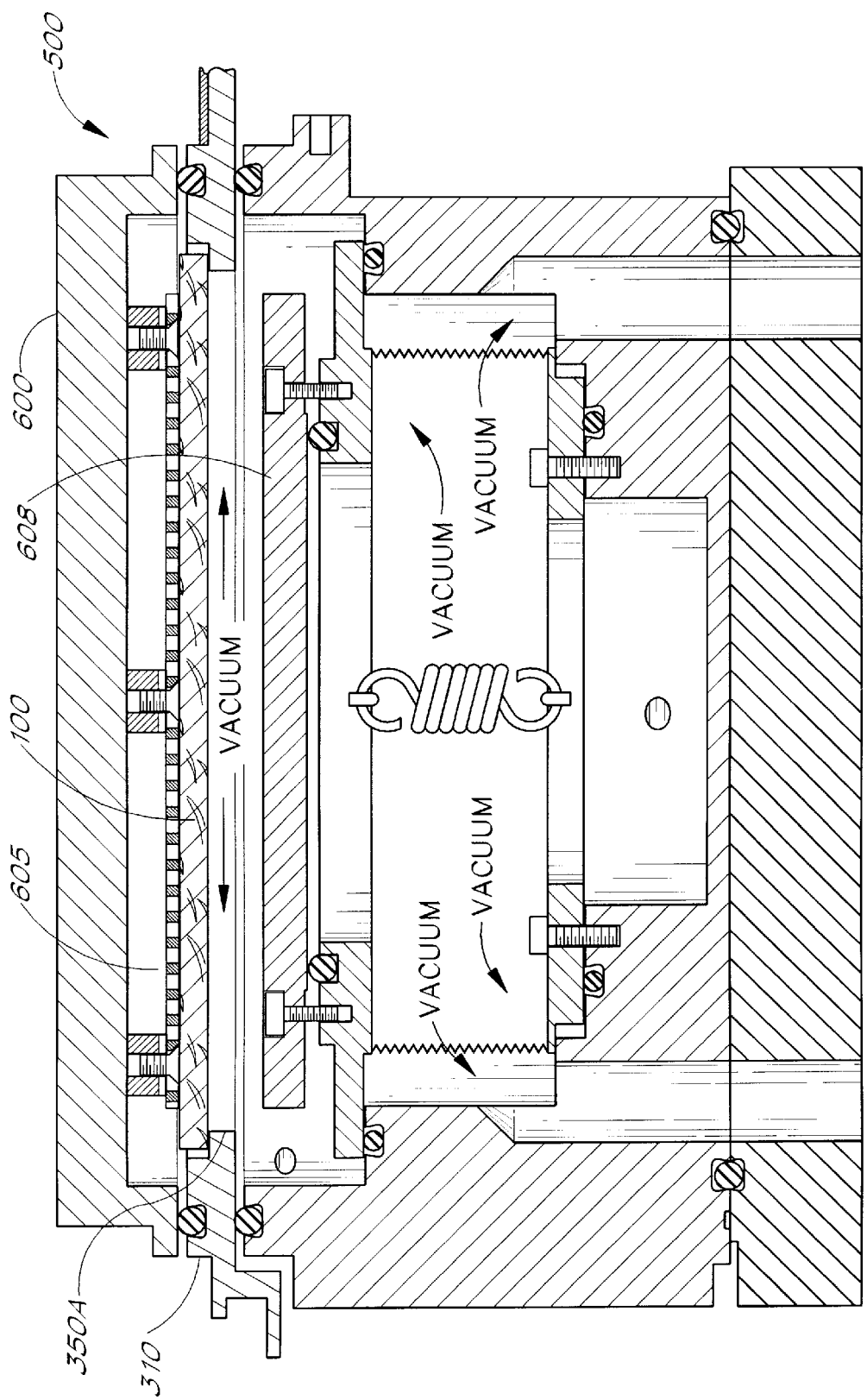
Figure 9C:
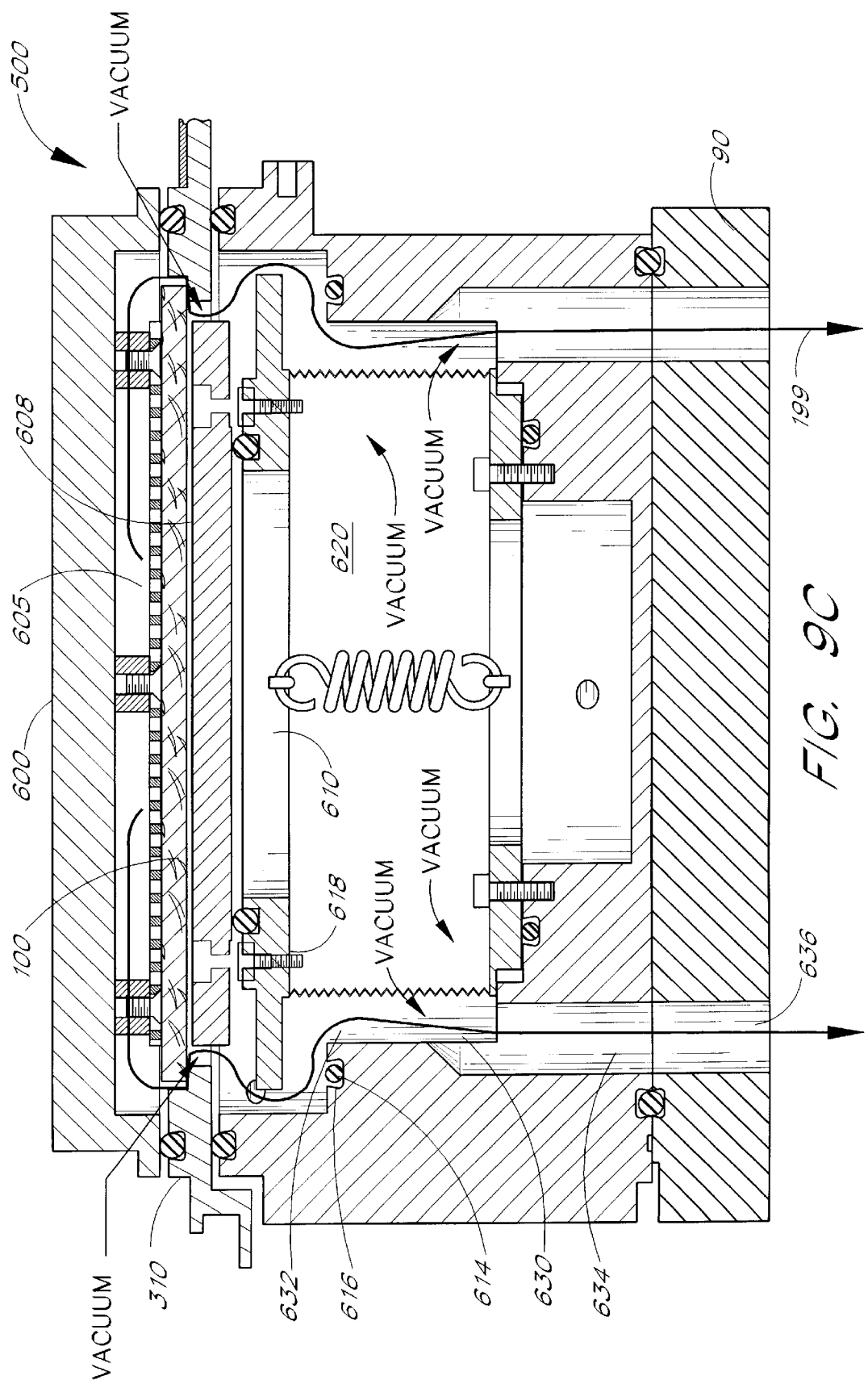

FIG. 8 illustrates the components of the injector 500 in greater detail. As described above, the injector 500 receives a peroxide disk 100 from the delivery system 300 in the manner described above. The injector housing 601 defines an aperture 602 of a chamber 604 formed within the housing 601 that is configured to receive the peroxide disk 100. A movable hot plate assembly 606 is positioned within the chamber 602. The movable hot plate assembly 606 includes a hot plate 608 that will heat the peroxide disk 100 to produce peroxide gas, in a manner that will be described hereinbelow, and a carriage assembly 610 that is movable between a sealed position, as shown in FIG. 8, and an open position as shown in FIG. 9C. As shown in FIG. 8, the hot plate 608 is bolted to the carriage assembly 610 via bolts 609. The carriage assembly 610 includes an annular flange 612 that is in communication with an o-ring 614 positioned on a bottom surface 616 of the chamber 604 when the carriage assembly 610 is in the sealed position.

As will be described in greater detail hereinbelow, the carriage assembly 610 is slidably movable towards the peroxide disk 100. In particular, a bellows chamber 620 is also formed within the housing 601 so as to be positioned underneath a bottom surface 618 of the carriage assembly 610. The bellows chamber 620 can be alternatively placed under vacuum or exposed to the air. When the bellows chamber 620 is placed under vacuum, the carriage assembly 610 is urged into the sealed position wherein the flange 612 is in sealed contact with the o-ring 614. The chamber 604 can also be placed under vacuum which results in the carriage 610 being urged towards the peroxide disk 100 when there is a higher pressure in the bellows chamber 620. In a preferred embodiment using a stainless steel bellows and carriage 610, at least a 500 Torr differential is preferred when a spring 638 is provided. This results in the flange 612 disengaging from the o-ring 614.

A plurality of communication passageways 630 are formed in the housing 601 positioned outward of the bellows chamber 620. The communication passageways 630 have an opening 632 that is positioned on the bottom surface 616 of the bellows chamber 604 inward of the o-ring 614. The communication passageways 630 have an opening 634 at the end opposite the opening 632 that is in communication with an access opening 636 in the wall of the sterilization chamber 90.

A spring 638 is attached between a bottom plate 640 of the bellows chamber and the carriage 610. The bottom plate 640 is attached to the housing 601 via bolts 642 in the manner shown in FIG. 8. The spring 638 biases the carriage 610 into the sealed position shown in FIG. 8 wherein the flange 612 is in contact with the o-ring 614.

The operation of the injector 500 will now be described in reference to FIGS. 9A–9E. In particular, a peroxide disk 100 that is captured within the aperture 350A of the lower carousel 310 is initially positioned within the aperture 602 in the manner that is described above. Simultaneously, the lid 600 that is captured within the upper carousel 220 is then positioned over the aperture 602 in the manner described above so that the disk 100 is sealed within the chamber 604. At this time, the chamber 604 is not under vacuum but the bellows chamber 620 is under vacuum as is shown in FIG. 9A. Consequently, the carriage 610 is positioned in the sealed position wherein the annular flange 612 is in contact with the o-ring 614.

Subsequently, as is shown in FIG. 9B, the chamber 604 is evacuated, then air is introduced into the bellows chamber 620. As shown in FIG. 9C, this results in the carriage assembly 610 moving upwards towards the peroxide disk 100 as a result of the chamber 604 being under vacuum and the bellows chamber 620 now being at atmospheric pressure. This results in the hot plate 608 contacting the peroxide disk 100 pressing against the perforated plate 605 which results in peroxide gas being produced. In the preferred embodiment, the surface of the disk 100 adjacent the hot plate 608 is the foil 106 (FIG. 2A) which preferably reflects the heat of the hot plate away from the disk 100 until the plate actually comes in contact with the disk 100.

Further, as is shown in FIG. 9C, the movement of the carriage 610 has resulted in the annular flange 612 disengaging from the o-ring 614 on the bottom surface 618 of the chamber 604. Consequently, the passages 630 now provide communication between the chamber 604 and the sterilization chamber 90.

Figure 9D:
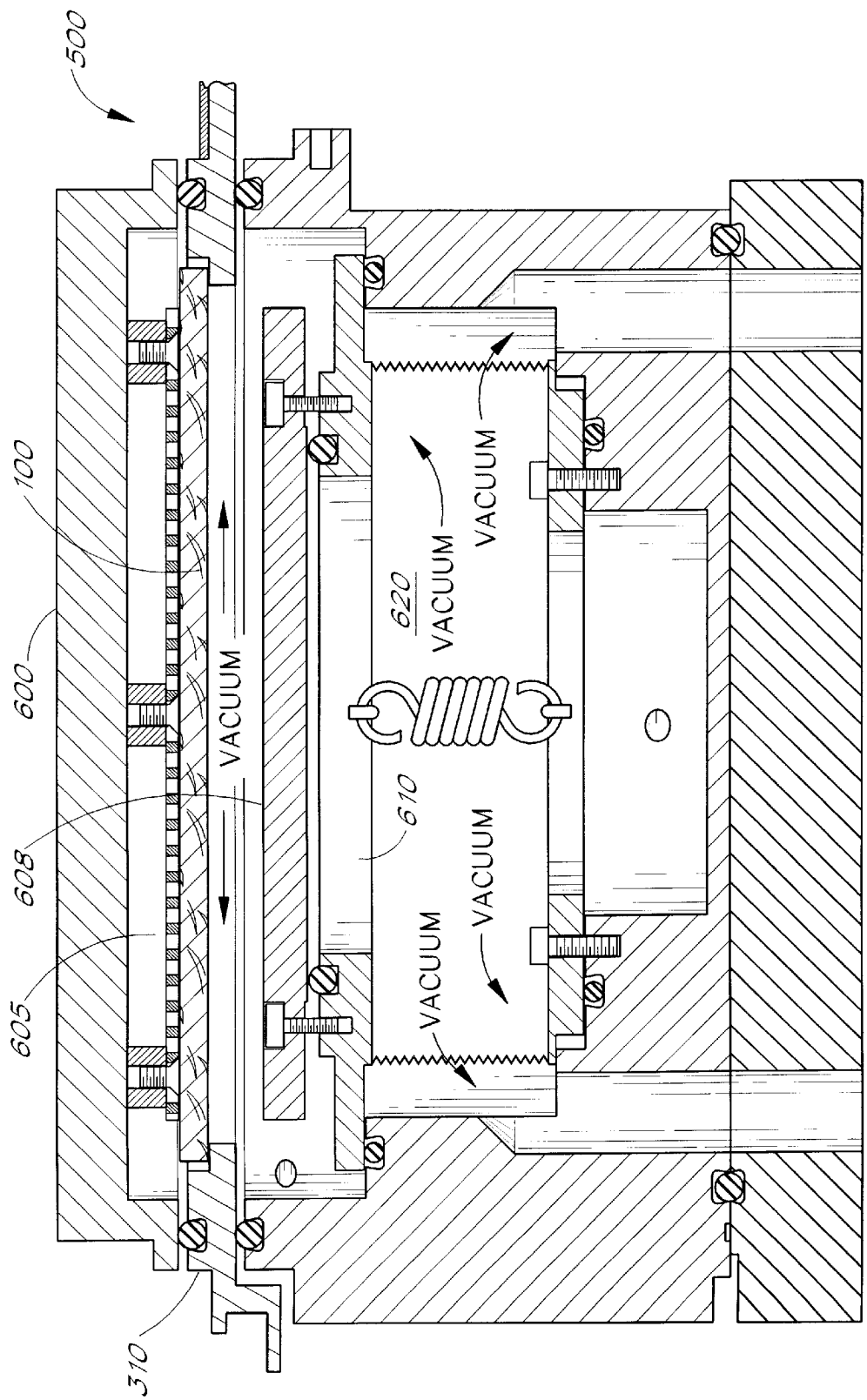
Figure 9E:
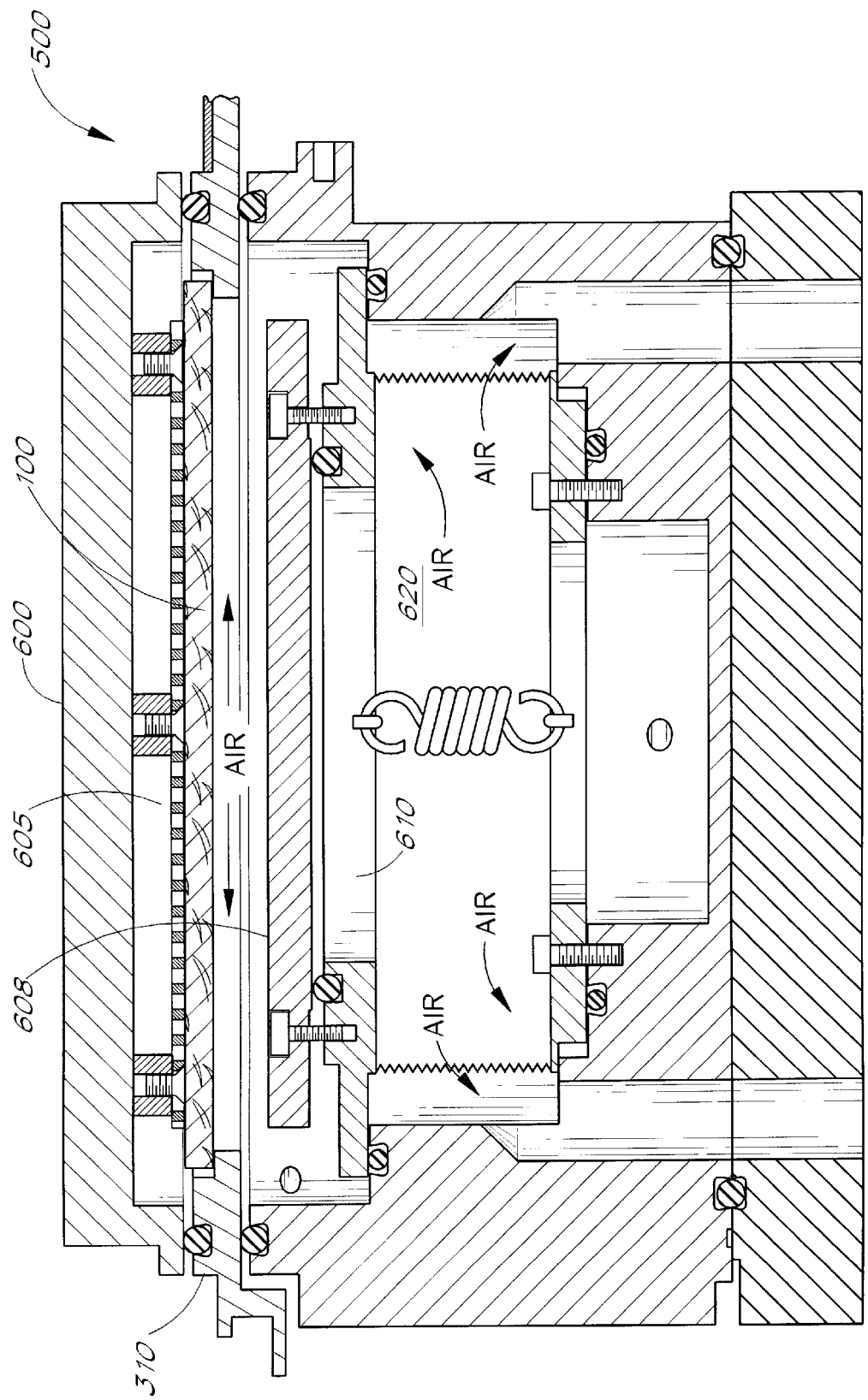

As the sterilization chamber 90 is under vacuum, the peroxide gas that is produced as a result of hot plate 608 contacting the peroxide disk 100 travels through the passageways 630 through a flow path 199 into the chamber 90 that contains the implements to be sterilized. Once the injection process is complete, the bellows chamber 620 is then placed under vacuum as is indicated in FIG. 9D. The combination of the vacuum in the bellows chamber 620 and the spring 638 result in the carriage 610 moving back into the sealed position wherein the flange 618 is in contact with the o-ring 614. The spring 638 is used to assure a rest position for the carriage 610. The chamber 604 can then be exposed to air which releases the seal between the upper carriage plate 610 and the injector housing 601 thereby permitting removal of the used peroxide disk 100 in the manner described hereinabove. The process can then be repeated with an additional peroxide disk in the same manner.

Hence, the system of the preferred embodiment allows for an automated sterilization of multiple batches of objects. The operator simply has to insert a disk laden cartridge 200 into the upper carousel 220 and an empty cartridge 200, and then initiate the sequence. The controller 50 sterilize a batch of objects position to sterilize a batch of objects positioned within the sterilization chamber 90, rotate and lower the carousels 220, 310 and initiate the vacuum means 418A, 418B so that a peroxide disk 100 is positioned within an aperture 350A–350C in the lower carousel 310. The controller then rotates the lower carousel 310 such that the aperture 350 is positioned over the aperture 602 in the housing 601 of the injector 500 and below the lid 600. During this step, the upper carousel 220 is preferably oriented so that the injector lid 600 is also positioned over the aperture 602 in the injector housing 601. The upper and lower carousels 220, 310 are then moved so that the disk 100 is positioned within the injector 500 in a sealed relationship.

The controller 50 then induces the injector 500 to heat the disk 100 by subjecting the chamber 604 to vacuum and releasing the vacuum within the bellows chamber 620. This results in the hot plate moving towards and contacting the disk 100 which results in the production of peroxide gas. The movement of the carriage 610 also preferably opens passageways to the chamber 90 so that the peroxide gas can be circulated into the chamber 90 to sterilize the objects.

Once the controller 50 determines that the injection cycle is complete, the hot plate 608 is retracted and the upper carousel 220 is removed to remove the injector lid 600. The lower carousel 310 is also preferably moved upward to extract the used disk 100 out of the injector 500. The lower carousel 310 and the upper carousel 220 are then moved relative to each other so that the destination cartridge 200 is located on the upper carousel 220 above the used disk 100 on the lower carousel 310. The carousels 220, 310 are then lowered by the controller 50 and the vacuum system 418 is activated to position the used disk in the destination cartridge.

It will be appreciated that the system of the preferred embodiment allows for the user to perform multiple sterilization sequences without reloading the system. Further, the system is entirely automated and has the benefit of using solid containers of hydrogen peroxide complex to release hydrogen peroxide vapor. Although the system 80 of the present invention uses a hot plate to heat the peroxide disk 100, alternative heating methods may also be used with this system. As discussed above, these alternative heating methods preferably make use of various alternative embodiments of the peroxide container 100.

Although the preferred embodiment of the present invention has shown, described and pointed out the fundamental novel features of the invention as applied to these embodiments, it will be understood that various omissions, substitutions and changes in the form of the detail of the device illustrated, may be made by those skilled in the art without departing from the spirit of the present invention. Consequently, the scope of the invention should not be limited to the foregoing discussion but is to be defined by the claims which follow.

What is claimed is:

1. A package for containing a solid material which releases hydrogen peroxide vapor upon heating, comprising:

a gas permeable, liquid impermeable membrane; and a solid hydrogen peroxide complex as solid material which releases hydrogen peroxide vapor upon heating, wherein said solid material is sealed in fluid communication with said gas permeable, liquid impermeable membrane such that the vapor released from said solid material is released through said membrane.

2. The package of claim 1, additionally comprising a conductive foil, wherein said solid material is between said gas permeable, liquid impermeable membrane and said conductive foil.

3. The package of claim 1, additionally comprising an impermeable membrane, wherein said solid material is between said gas permeable, liquid impermeable membrane and said impermeable membrane.

4. The package of claim 3, wherein said impermeable membrane is of Mylar™, polycarbonate or PTFE material.

5. The package of claim 1, additionally comprising a perforated material or screen outside of the gas permeable, liquid impermeable membrane.

6. The package of claim 1, additionally comprising a screen adjacent said solid material, said screen providing pockets holding said solid material.

7. The package of claim 6, wherein said screen is conductive of heat so as to improve heat transfer to said solid material.

8. The package of claim 1, wherein said solid material is in the form of a powder, tablet or dried slurry.

9. The package of claim 1, additionally comprising an impermeable material sealed over said gas permeable, liquid impermeable membrane, such that said solid material will be sealed within said package until said impermeable material is ruptured.

10. The package of claim 1, wherein the package is incorporated into a support which can be handled.

11. The package of claim 10, wherein the support forms a seal to enclose said solid material.

12. The package of claim 10, wherein the support has perforations around the package, said perforations configured to permit gas or vapor released from said solid material and through said gas permeable, liquid impermeable membrane to be delivered to an opposing side of said package.

13. The package of claim 1, wherein the gas permeable, liquid impermeable material is heat-sealed to enclose said solid material.

14. A cartridge housing which comprises a plurality of packages for containing a solid material which releases hydrogen peroxide vapor upon heating, each of said packages comprising:

a gas permeable, liquid impermeable membrane; and a solid hydrogen peroxide complex as said solid material which releases hydrogen peroxide vapor upon heating, wherein said solid material is sealed in fluid communication with said gas permeable, liquid impermeable membrane such that the vapor released from said solid material is released through said membrane.

15. The cartridge housing of claim 14, wherein the plurality of packages are stacked so that each of said packages can be activated one at a time.

16. The cartridge housing of claim 14, wherein each of said packages has at least one edge joined to at least one edge of another of said packages.

17. The cartridge housing of claim 14, wherein the plurality of packages are folded in a Z-fold.

18. The cartridge housing of claim 14, wherein the plurality of packages are rolled.

19. The cartridge housing of claim 18, wherein the plurality of packages are rolled onto a core.

20. The cartridge housing of claim 14, wherein the packages are arranged around the periphery of a disk.

21. The cartridge housing of claim 14, wherein the packages are sealed within the housing.

22. The cartridge housing of claim 21, configured to trap gas or vapor released from said solid material within the housing.

23. The cartridge housing of claim 21, additionally comprising an impermeable material sealed over the housing, such that said packages will be sealed within said housing until said impermeable material is ruptured.

24. The cartridge housing of claim 14, wherein the housing is adapted to protect the packages therewithin from a heating source.

* * * * *